US012297413B2

(12) United States Patent
Murthy et al.

(10) Patent No.: US 12,297,413 B2
(45) Date of Patent: *May 13, 2025

(54) SYSTEMS AND METHODS FOR CELL CULTURING

(71) Applicant: FLASKWORKS, LLC, Boston, MA (US)

(72) Inventors: Shashi K. Murthy, Newton, MA (US); Andrew Kozbial, East Boston, MA (US)

(73) Assignee: FLASKWORKS, LLC, Boston, MA (US)

( * ) Notice: Subject to any disclaimer, the term of this patent is extended or adjusted under 35 U.S.C. 154(b) by 371 days.

This patent is subject to a terminal disclaimer.

(21) Appl. No.: 17/842,212

(22) Filed: Jun. 16, 2022

(65) Prior Publication Data

US 2022/0306977 A1 Sep. 29, 2022

Related U.S. Application Data

(63) Continuation of application No. 17/074,921, filed on Oct. 20, 2020.

(60) Provisional application No. 62/923,978, filed on Oct. 21, 2019, provisional application No. 62/923,975, filed on Oct. 21, 2019, provisional application No. 62/923,967, filed on Oct. 21, 2019, provisional application No. 62/923,963, filed on Oct. 21, 2019, provisional application No. 62/923,982, filed on Oct. 21, 2019, provisional application No. 62/923,973, filed on Oct. 21, 2019.

(51) Int. Cl.

| | | |
|---|---|---|
| *C12N 5/02* | (2006.01) |
| *A01N 1/02* | (2006.01) |
| *A61K 35/17* | (2015.01) |
| *C12M 1/00* | (2006.01) |
| *C12M 1/04* | (2006.01) |
| *C12M 1/12* | (2006.01) |
| *C12M 1/26* | (2006.01) |
| *C12M 1/34* | (2006.01) |
| *C12M 1/36* | (2006.01) |
| *C12M 1/42* | (2006.01) |
| *C12M 3/00* | (2006.01) |
| *C12N 5/00* | (2006.01) |
| *C12N 5/0783* | (2010.01) |
| *C12N 5/0784* | (2010.01) |

(52) U.S. Cl.
CPC ............ *C12M 23/58* (2013.01); *A01N 1/0221* (2013.01); *A61K 35/17* (2013.01); *C12M 23/24* (2013.01); *C12M 23/48* (2013.01); *C12M 29/00* (2013.01); *C12M 29/10* (2013.01); *C12M 29/14* (2013.01); *C12M 33/12* (2013.01); *C12M 35/08* (2013.01); *C12M 37/04* (2013.01); *C12M 41/14* (2013.01); *C12M 41/34* (2013.01); *C12M 41/48* (2013.01); *C12M 45/22* (2013.01); *C12N 5/00* (2013.01); *C12N 5/0636* (2013.01); *C12N 5/0637* (2013.01); *C12N 5/0638* (2013.01); *C12N 5/0639* (2013.01); *C12N 2501/998* (2013.01); *C12N 2502/1121* (2013.01); *C12N 2502/1157* (2013.01)

(58) Field of Classification Search
None
See application file for complete search history.

(56) References Cited

U.S. PATENT DOCUMENTS

| | | |
|---|---|---|
| 3,848,569 A | 11/1974 | Folsom |
| 3,907,687 A | 9/1975 | Hoeltzenbein |
| 4,939,151 A | 7/1990 | Bacehowski et al. |
| 5,536,662 A | 7/1996 | Humphries et al. |
| 5,612,188 A | 3/1997 | Shuler et al. |
| 5,656,155 A | 8/1997 | Norcross et al. |
| 5,801,054 A | 9/1998 | Kiel et al. |
| 6,403,369 B1 | 6/2002 | Wood |
| 6,410,309 B1 | 6/2002 | Barbera-Guillem et al. |
| 6,607,910 B1 | 8/2003 | Dimitrijevich et al. |
| 2002/0041868 A1 | 4/2002 | Nicolette et al. |
| 2002/0110905 A1 | 8/2002 | Barbera-Guillem et al. |
| 2003/0036192 A1 | 2/2003 | Singh |
| 2004/0091479 A1 | 5/2004 | Nieland et al. |
| 2005/0003533 A1 | 1/2005 | Kalinski |
| 2005/0014129 A1 | 1/2005 | Cliffel et al. |

(Continued)

FOREIGN PATENT DOCUMENTS

| | | |
|---|---|---|
| AU | 2012/205259 A1 | 8/2012 |
| CA | 2905786 A1 | 10/2014 |

(Continued)

OTHER PUBLICATIONS

Bajgain, 2014, Optimizing the production of suspension cells using the G-Rex "M" series, Molecular Therapy—Methods & Clinical Development, 1(14015):1-9.
Carrier, 2002, Perfusion improved tissue architecture of engineered cardiac muscle, Tissue Eng, 8(2): 175-188.
Fiedler, 1998, Dielectrophoretic Sorting of Particles and Cells in a Microsystem, Analytical Chemistry 70:1909-15.
Fulwyler, 1965, Electronic Separation of Biological Cells by vol. Science 150(3698):910-11.

(Continued)

*Primary Examiner* — Michail A Belyavskyi
(74) *Attorney, Agent, or Firm* — Brown Rudnick LLP; Adam M. Schoen

(57) ABSTRACT

Cell culture systems and methods provide improved immunotherapeutic product manufacturing with greater scalability, flexibility, and automation. Cell culture systems are configured with interchangeable cartridges, allowing versatility and scalability. Systems are configured to have multiple connected cell culture chambers, which allows parallel processing of different types of cells. Gas-impermeable cell culture chambers and methods for generating cells in closed systems prevent contamination and user error. Methods for recycling cell culture medium provide additional efficiencies.

18 Claims, 11 Drawing Sheets

(56) References Cited

U.S. PATENT DOCUMENTS

| | | |
|---|---|---|
| 2005/0186669 A1 | 8/2005 | Ho et al. |
| 2005/0211373 A1 | 9/2005 | Tomasetti et al. |
| 2006/0019385 A1 | 1/2006 | Smith et al. |
| 2006/0099177 A1 | 5/2006 | June et al. |
| 2006/0115893 A1 | 6/2006 | Kobayashi et al. |
| 2007/0134790 A1 | 6/2007 | Gould et al. |
| 2007/0161051 A1 | 7/2007 | Tsinberg et al. |
| 2008/0032380 A1 | 2/2008 | Kleis et al. |
| 2008/0032398 A1 | 2/2008 | Cannon et al. |
| 2008/0227176 A1 | 9/2008 | Wilson |
| 2009/0075360 A1 | 3/2009 | Ho et al. |
| 2009/0155908 A1 | 6/2009 | Halberstadt et al. |
| 2009/0162853 A1 | 6/2009 | Clark et al. |
| 2010/0055776 A1 | 3/2010 | Weibezahn et al. |
| 2010/0075293 A1 | 3/2010 | Chang et al. |
| 2010/0248344 A1 | 9/2010 | Schroder et al. |
| 2012/0077243 A1 | 3/2012 | Niazi |
| 2012/0224450 A1 | 9/2012 | Priestman |
| 2012/0277652 A1 | 11/2012 | Zhao |
| 2013/0095566 A1 | 4/2013 | Oltvai et al. |
| 2013/0161229 A1 | 6/2013 | Barbaroux et al. |
| 2013/0309771 A1 | 11/2013 | Gevaert et al. |
| 2014/0065660 A1 | 3/2014 | Kim et al. |
| 2014/0193374 A1 | 7/2014 | Zhao et al. |
| 2014/0295541 A1 | 10/2014 | Nakanishi et al. |
| 2015/0158907 A1 | 6/2015 | Zhou et al. |
| 2015/0204767 A1 | 7/2015 | Taniguchi |
| 2016/0122782 A1 | 5/2016 | Crisman et al. |
| 2016/0145563 A1 | 5/2016 | Berteau et al. |
| 2016/0178490 A1 | 6/2016 | Civel et al. |
| 2016/0215246 A1 | 7/2016 | Goh et al. |
| 2016/0272934 A1 | 9/2016 | Chander et al. |
| 2016/0361360 A1 | 12/2016 | Chang et al. |
| 2017/0042770 A1 | 2/2017 | Warner et al. |
| 2017/0051238 A1 | 2/2017 | Tanaka et al. |
| 2017/0112911 A1 | 4/2017 | Sahin et al. |
| 2017/0175073 A1 | 6/2017 | Lipkens et al. |
| 2018/0171296 A1 | 6/2018 | Murthy et al. |
| 2018/0251723 A1 | 9/2018 | Murthy |
| 2019/0177692 A1 | 6/2019 | June et al. |
| 2020/0157484 A1 | 5/2020 | Kozbial |
| 2020/0231918 A1 | 7/2020 | Kozbial |
| 2020/0308523 A1 | 10/2020 | Murthy |
| 2020/0385678 A1 | 12/2020 | Murthy et al. |
| 2021/0213010 A1 | 7/2021 | Andresen et al. |

FOREIGN PATENT DOCUMENTS

| | | |
|---|---|---|
| CN | 105907641 B | 6/2018 |
| EP | 1392814 B1 | 6/2007 |
| EP | 2 623 587 A1 | 8/2013 |
| GB | 2062006 A | 5/1981 |
| JP | 2010/200693 A | 9/2010 |
| WO | 2003/010292 A2 | 2/2003 |
| WO | 2005/113742 A1 | 12/2005 |
| WO | 2009/104296 A1 | 8/2009 |
| WO | 2016/100923 A1 | 6/2016 |
| WO | 2017/004169 A1 | 1/2017 |
| WO | 2017/079674 A1 | 5/2017 |
| WO | 2018/005521 A2 | 1/2018 |
| WO | 2018/041423 A1 | 3/2018 |

OTHER PUBLICATIONS

Gu, 2004, Computerized microfluidic cell culture using elastomeric channels and Braille displays, PNAS, 101(45):15861-15866.
International Search Report and Written Opinion issued in International Application No. PCT/US2020/055792, date of mailing: Jan. 26, 2021, 25 pages.
Kashaninejad, 2016, Organ-Tumor-on-a-Chip for Chemosensitivity Assay, Micromachines, 7 (130):1-24.
Korin, 2008, Periodic 'Flow-Stop' Perfusion Microchannel Bioreactors for Mammalian and Human Embryonic Stem Cell Long-Term Culture, Biomedical Microdevices, 11(1): 87-94.
Kozbial, 2018, Automated Generation of Immature Dendritic Cells in a Single-Use System, J. Immunol Methods, vol. 457, pp. 53-65.
Kozbial, 2018, Scale-up of a perfusion-based dendritic cell generation process, Cell & Gene Therapy Insights, 4:1117-1130.
Lexico Dictionary definition of concurrent.
Li, 1997, Transport, Manipulation, and Reaction of Biological Cells On-Chip Using Electrokinetic Effects, Analytical Chemistry 69:1564-1568.
Nino, 2016, Antigen-specific T cells fully conserve antitumour function following cryopreservation, Immunology and Cell Biology, 94:411-418.
Rosenblatt, 2011, Vaccination with dendritic cell/tumor fusion cells results in cellular and humeral antitumor immune responses in patients with multiple myeloma, Blood, 117(2):393-402.
Rothbauer, 2018, Recent advances in microfluidic technologies for cell-to-cell interaction studies, Lab on a chip, 18:249-270.
Rowjewski, 2013, GMP-Compliant Isolation and Expansion of Bone Marrow-Derived MSCs in the Closed, Automated Device Quantum Cell Expansion System, Cell Transplantation, 22(11):1981-2000.
Sakar, 2003, Caspase-mediated apoptosis and cell death of rhesus macaque CD4+ T-cells due to cryopreservation of peripheral blood mononuclear cells can be rescued by cytokine treatment after thawing. Academic Press. Cryobiology, 47:44-58.
Sattui, 2012, Cryopreservation modulates the detection of regulatory T cell markers, Clinical Cytometry, 82B:54-58.
Schurlein, 2017, A versatile modular bioractor platform for Tissue Engineering, Biotechnol. J., 12:1600326, 13 pages.
Tai, 2018, Molecular Mechanisms of T Cells Activation by Dendritic Cells in Autoimmune Diseases, Frontiers in Pharmacology, 9(642):1-10.
Valitutti, 2010, The space and time frames of T cell activation at the immunological synapse, FEBS Letters, 584:4851-4857.
Gibco (AIM-V Medium CTS, 2010 pp. 1-2).

SYSTEMS AND METHODS FOR CELL CULTURING

CROSS-REFERENCE TO RELATED APPLICATIONS

This application is a continuation of U.S. application Ser. No. 17/074,921, filed Oct. 20, 2020, now allowed, which claims priority to, and the benefit of, U.S. Provisional Application No. 62/923,963, filed Oct. 21, 2019, and to U.S. Provisional Application No. 62/923,967, filed Oct. 21, 2019, and to U.S. Provisional Application No. 62/923,973, filed Oct. 21, 2019, and to U.S. Provisional Application No. 62/923,975, filed Oct. 21, 2019, and to U.S. Provisional Application No. 62/923,978, filed Oct. 21, 2019, and to U.S. Provisional Application No. 62/923,982, filed Oct. 21, 2019, the contents of which are incorporated by reference herein in their entirety.

FIELD OF THE INVENTION

The present disclosure relates generally to systems and methods for cell culturing.

BACKGROUND

Cancer is a leading cause of mortality and morbidity worldwide, and despite years of extraordinary research efforts, treatments have remained elusive. The diversity of tumor types presents a challenge in cancer therapy, as treatments tailored to one tumor may not be effective against another. Personalized treatments have been sought, but many challenges exist in developing them.

One promising area has been T cell therapy, wherein a patient's T cells are altered to target certain cancers. This includes chimeric antigen receptor T cell (CAR-T) therapy, T cell receptor (TCR) therapy, and neoantigen-based T cell therapy. Neoantigen-based therapies provide the ability to identify antigens from tumor sequencing data to design highly personalized patient-specific immunotherapies.

Unfortunately, many challenges exist in the development and manufacture of T cell therapies. Existing processes for isolation, preparation, and expansion of cancer antigen-specific T-cells are limited. Conventional protocols for stimulation of human T cells by autologous antigen-presenting dendritic cells (DCs) involve several manual steps, including transferring cells between culture vessels, changing media, and replenishing cytokines and cell medium. Those processes are labor-intensive and not readily scalable. The number of manual steps required to carry out the protocol is prohibitively high. Additionally, those protocols involve the use of flasks or other containers, which are opened and closed during use, adding to the risk of contamination which can compromise the quality and safety of the cell product. Such methods do not comply with current good manufacturing practices (cGMP) and are not useful for producing T cell therapies at large scale. Additional challenges also exist, such as time of cell preparation, maintenance of optimal phenotype, expansion to sufficient cell number, and quality and safety of the cell product.

SUMMARY

The invention recognizes that automating T cell therapy processing and manufacturing has been unsuccessful due to the complex biological processes associated as well as the bioprocess and regulatory requirements associated with autologous cell processing. The few systems that do exist are overly complex and cost-prohibitive, and are therefore are not useful for pre-clinical assays. The inventive cell culture systems and related methods of the invention provide solutions to many of the problems in cell culturing and provides numerous features to decrease contamination and user error, as well as increase efficiency, scalability, and ease of use. The systems and methods of the invention provide capabilities for robust T cell production, while minimizing cost and increasing simplicity and ease of use, making the disclosed systems and methods useful for both pre-clinical research and routine cell culture, while being capable of meeting requirements for current good manufacturing practices for clinical manufacturing.

In certain aspects, the disclosed systems and methods provide improved automated technology for producing antigen-specific T cells. Automation of the manual processes dramatically reduces opportunities for user error and decreases the risk of contamination. For example, the disclosure provides systems and methods for producing CAR-T and TCR transduced T cells, as well as neoantigen-targeting T cells in a closed system. This avoids the need to open and close T flasks, as is common in the prior art, thereby simplifying the process and avoiding sources of contamination. As another example, cell culture systems are disclosed which are configured with easily interchangeable cell culture chambers, allowing the user to scale up or scale down a cell population. The various chambers and vessels are connectable via sterile tube welding, so that the system can remain closed throughout use. The disclosure also provides gas-impermeable cartridges for cell culture, which provide a solid polystyrene surface for optimal cell adhesion and rigid cartridge construction which is easy to manufacture and less susceptible to contamination when operated with welded tube connections. The disclosed systems also allow parallel processing of dendritic cells and T cells in a process for generating stimulated T cells. The system architecture streamlines the process of T cell culture, providing savings in time and materials. Another way that the system saves materials is by recycling cell culture medium, to ensure that cells can be cultured with minimal amount of expensive culture medium and supplements.

In addition to the features described above, other features will be apparent to those of skill in the art, as the disclosed systems and methods provide numerous opportunities for process optimization in immunotherapeutic product manufacturing.

Aspects of the disclosure provide a cell culture system with interchangeable cartridges. The cell culture system includes a first area configured to receive a fluid reservoir containing a cell culture medium and a second area configured to receive a waste reservoir. The cell culture system also has one or more pumps fluidically connectable to the fluid reservoir and a substrate configured to receive and retain cell culture chambers of different shapes and/or sizes.

In embodiments, the substrate has a plurality of different openings arranged such that the substrate is configured to receive and retain cell culture chambers of different shapes and/or sizes. The substrate can be configured to receive and retain multiple cell culture chambers simultaneously. A first portion of the substrate may be configured to receive a first cell culture chamber of a first size whereas a second portion of the substrate is configured to receive a second cell culture chamber of a second shape which is different from the first size. In embodiments, the first portion of the substrate is configured to receive a first cell culture chamber of a first shape and the second portion of the substrate is configured to receive a second cell culture chamber of a second shape that is different from the first shape. In embodiments, the first portion of the substrate is configured to receive a first cell culture chamber of a first size and shape and a second portion of the substrate is configured to receive a second cell culture chamber of a second size and shape that is different from the first size and shape.

In embodiments, the fluid reservoir is positioned in the first area and the waste reservoir is positioned in the waste area. One or more tubes can be included that fluidically connect the fluid reservoir to the one or more pumps, and/or the one or more pumps to the cell culture chambers, and/or the cell culture chambers to the waste reservoir. Each cell culture chamber can be fluidically coupled to a separate pump. In some embodiments, a processor is operably connected to the one or more pumps and one or more sensors are operable to measure a characteristic of a fluid in the cell culture system, wherein the processor operates the one or more pumps based on the measured characteristic.

In a related aspect, the disclosure provides a method for culturing cells. The method includes providing a cell culture system that has a first area configured to receive a fluid reservoir containing a cell culture medium and a second area configured to receive a waste reservoir, one or more pumps fluidically connectable to the fluid reservoir, and a substrate configured to receive and retain cell culture chambers of different shapes and/or sizes. The method further involves loading the fluid reservoir into the first area and the waste reservoir into the second area, loading a first cell culture chamber of a first size and/or shape onto a first portion of the substrate, and loading a second cell culture chamber of a second size and/or shape onto a second portion of the substrate. The method further involves connecting the fluid reservoir, the one or more pumps, the first and second cell culture chambers, and the waste reservoir with tubing. The method further involves operating the system to culture cells in the first and second cell culture chambers.

In embodiments, the substrate has a plurality of different openings arranged such that the substrate is configured to receive and retain cell culture chambers of different shapes and/or sizes. The first cell culture chamber can be of a first size and the second cell culture chamber can be of a second size. The first cell culture chamber can be of a first shape and the second cell culture chamber can be of a second shape. The first cell culture chamber can be of both a first size and shape, and the second cell culture chamber can be of both a second size and shape.

In embodiments, each of the first and second cell culture chambers is fluidically coupled to a separate pump. The system can also include a processor operably connected to the one or more pumps and one or more sensors operable to measure a characteristic of a fluid in the cell culture system, wherein the processor operates the one or more pumps based on the measured characteristic.

In embodiments, after cell culturing is complete in the first and second cell culture chambers, the cultured cells in each of the first and second cell culture chambers are collected. The cultured cells in each of the first and second cell culture chambers can be collected in the same collection vessel or in different collection vessels.

In another aspect, the disclosure provides a method for producing transduced T cells with CAR or TCR in a closed system. The method involves providing a cell culture instrument that has first and second culture chambers and flowing a suspension containing cells into the first culture chamber. The method further involves perfusing the T cells in the first culture chamber with appropriate transduction and expansion reagents to produce transduced T cells which expand in the first culture chamber. The method further involves flowing the transduced and expanded T cells from the first culture chamber into the second culture chamber. The method further involves flowing a cell culture medium into the second culture chamber to further expand the transduced and expanded T cells, wherein the method is performed on a single instrument in a closed manner such that sterility is maintained throughout the method.

In some embodiments, the second culture chamber is larger than the first culture chamber. One or both culture chambers can be made of polystyrene. The culture chambers can be connected via a sterile tube. The first culture chamber may have an activation reagent and/or a cell transduction reagent, which may be an inactive virus expressing CAR or TCR. Alternatively the second culture chamber may be a separate cell culture instrument that is not part of the first cell culture instrument.

In embodiments, the cell culture medium is provided in a sterile vessel and is connected to the closed system by sterile tube welding. Flowing the cell culture medium into the first culture chamber may involve eliminating headspace in the first culture chamber. The cell culture medium may include Aim V with interleukin-2.

The method may further involve activating the T cells in the first culture chamber, which can be done by contacting with a magnetic or non-magnetic bead comprising one or more activating antibodies or soluble activation antibody-containing reagents, and a transduction reagent. The method may further involve draining fluid from the second culture chamber, washing the transduced and expanded T cells with a buffer, and flowing a cryopreservation medium into the second culture chamber to re-suspend the transduced and expanded T cells. the method may further involve flowing the transduced and expanded T-cells into a harvesting vessel in a closed manner.

In embodiments, each of the flowing steps may be done via sterile tubes. The sterile tubes may be connected by sterile tube welding.

In another aspect, the disclosure provides a method for producing neoantigen-targeting T cells in a closed system. The method includes providing a cell culture instrument having first and second culture chambers and flowing cell culture medium containing monocytes into the first culture chamber. The method also involves perfusing the purified monocytes in the first culture chamber to produce dendritic cells in the first culture chamber and contacting the dendritic cells with antigen material, which may include tumor-specific peptides, in the first culture chamber to produce mature dendritic cells. The method further involves flowing the mature dendritic cells from the first culture chamber into the second culture chamber comprising purified T cells to co-culture the mature dendritic cells and the purified T cells, to thereby produce neoantigen-targeting T cells. The method is performed on a single instrument in a closed manner such that sterility is maintained throughout the method.

In embodiments, the method also involves flowing a second batch of monocytes into the second culture chamber, differentiating them into dendritic cells and maturing the dendritic cells, in order to then perform a second co-culture with the purified T cells. The first and second culture chambers can be made of polystyrene. The first and second culture chambers can be connected via a sterile tube. The cell culture medium can be provided in a sterile vessel and can be connected to the closed system by sterile tube welding. The step of flowing the cell culture medium into the first culture chamber can involve eliminating headspace in the first culture chamber. Each of the flowing steps can be done via sterile tubes, which may be connected by sterile tube welding.

In embodiments, the method also includes activating the T cells in the second culture chamber. In embodiments, the method also includes draining fluid from the second culture chamber, washing the neoantigen-targeting T cells with a buffer, and flowing a cryopreservation medium into the second culture chamber to re-suspend the neoantigen-targeting T cells. The method may also involve flowing the neoantigen-targeting T cells into a harvesting vessel in a closed manner.

In another aspect, the disclosure provides a method for parallel processing to produce dendritic cells and stimulate T cells in parallel. The method includes providing a cell culture instrument with first and second culture chambers and flowing cell culture medium containing monocytes into the first culture chamber. The method further includes perfusing the monocytes in the first culture chamber to produce dendritic cells in the first culture chamber. The method further includes flowing T cells that have been cultured in the second culture chamber from the second culture chamber into the first culture chamber with the dendritic cells to further culture the T cells in the first culture chamber. In embodiments, sterility is maintained throughout the method.

The method may also include collecting the cultured T cells from the first culture chamber by flowing the cultured T cells into a collection vessel. The method may also include maturing the dendritic cells in the first culture chamber by contacting the dendritic cells with antigen material, which may include tumor-specific peptides. In embodiments, the method also involves activating the T cells in the second culture chamber, which can be done by using an activation reagent. In embodiments, the method also involves washing the stimulated T cells with a buffer, and optionally transferring the stimulated T cells to a cryopreservation medium. The method may also involve flowing the neoantigen-targeting T cells into a harvesting vessel in a closed manner. Each of the flowing steps can be done via sterile tubes, which are optionally connected by sterile tube welding.

The cell culture medium may be provided in a sterile vessel and may be connected to the closed system by sterile tube welding. Flowing the cell culture medium into the first culture chamber may involve eliminating headspace in the first culture chamber. In embodiments, the first and second culture chambers are made of polystyrene, and optionally may be connected via a sterile tube. In some embodiments, one or both of the first and second cell culture chambers from the cell culture instrument can be replaced and the method can be repeated.

In another aspect, the disclosure provides a gas-impermeable cell culture chamber, wherein a top, a bottom, and both side walls are comprised of a gas-impermeable material. The gas-impermeable material may also be a material to which cells adhere. The gas-impermeable material may be polystyrene.

In embodiments, the cell culture chamber has an inlet. The cell culture chamber may also have an outlet. The inlet and the outlet can be located on the top of the cell culture chamber, and optionally the inlet and the outlet are each configured to fluidically and sealably couple with tubing. The cell culture chamber can be integrally formed, and it can be sized and configured to fit within an incubator. The cell culture chamber can be sized and configured to couple to a substrate of a cell culture instrument.

In a related aspect, the disclosure provides a method for culturing cells that involves providing a cell culture chamber having an inlet and an outlet, wherein a top, a bottom, and both side walls are made of a gas-impermeable material. The method also involves loading cells in to the cell culture chamber and flowing a cell culture medium into the cell culture chamber via the inlet to culture the cells in the culture chamber and out of the cell culture chamber via the outlet, wherein the flowing of the cell culture medium through the cell culture chamber via the inlet and the outlet causes continuous flow of cell culture medium through the cell culture chamber and allows for gas exchange to occur between the cells in the cell culture chamber and the cell culture medium.

In embodiments, the gas-impermeable material is also a material to which cells adhere, such as polystyrene. In embodiments, the inlet and the outlet are located on the top of the cell culture chamber and are optionally configured to fluidically and sealably couple with tubing. The tubing can be high permeability tubing which allows the cell culture medium to exchange gas while in the high permeability tubing. In embodiments, the cell culture chamber is integrally formed. The cell culture chamber can be sized and configured to fit within an incubator and optionally it can be sized and configured to couple to a substrate of a cell culture instrument.

In another aspect, the disclosure provides a method for culturing cells that involves culturing cells in a cell culture chamber on a cell culture instrument by flowing a cell culture medium through the cell culture chamber, wherein a portion of the cell culture medium that has already been flowed through the cell culture chamber is recycled back into the cell culture chamber during the cell culturing process.

In embodiments, the method also involves measuring one or more parameters of the used medium prior to the recycling. The parameters can be a concentration of one or more compounds within the used medium, such as glucose, lactate, dissolved oxygen, or cell metabolites. The parameter can also be pH or cell number.

In embodiments, the method involves determining, using a processor operably connected to the cell culture chamber, whether at least one of the one or more parameters of the used medium meets a predetermined threshold prior to the recycling step. The measuring step can be performed by one or more sensors operably associated with the cell culture chamber. The one or more sensors can be operably associated with a waste reservoir in fluid communication with the cell culture chamber. The cell culture chamber can be operably connected to one or more pumps, and may have an inlet and an outlet. The recycling step may involve redirecting the portion of used medium from the waste reservoir back into the cell culture chamber. In embodiments, the portion of used medium is combined with a bolus of fresh medium.

In a related aspect, the disclosure provides a method for culturing cells, which involves providing a cell culture chamber containing cells, flowing a cell culture medium into the cell culture chamber, removing used cell culture medium from the cell culture chamber, assessing a parameter of the used cell culture medium, and returning the used cell culture medium to the cell culture chamber if the parameter meets a predetermined threshold.

In embodiments, the method also involves combining the used cell culture medium with a bolus of fresh cell culture medium prior to the returning step. The assessing step may involve measuring the parameter using a sensor operably coupled to the cell culture chamber. The assessing step may involve determining, using a processor, whether the parameter meets the predetermined threshold. The parameter may be a measured concentration of one or more compounds within the used cell culture medium, such as glucose, lactate, or cell metabolites. In embodiments, the returning step comprises redirecting the used cell culture medium from a waste reservoir into the cell culture chamber. In other embodiments, the method also involves discarding the used cell culture medium if the parameter does not meet the predetermined threshold, and flowing fresh cell culture medium into the cell culture chamber.

In another aspect, this disclosure provides a cell culture system that includes a plurality of shelves for receiving fluid reservoirs. The shelves may be stacked with a first shelf on top of a second shelf, each of the first and second shelves configured to receive a fluid reservoir. Each of the shelves may include a retaining mechanism that retains the fluid reservoir on each of the first and second shelves.

The system may further include at least one pump, a processor operably coupled to the at least one pump; and a substrate sized and configured to hold a plurality of cell culture chambers at a same time. Preferably, the system further includes at least one sensor, and the processor may be connected to the at least one sensor and can configured to operate the at least one pump based on a characteristic measured by the sensor. For example, the sensor may measure a concentration of one or more compounds within cell culture medium, such as glucose, lactate, or cell metabolites. The processor may regulate the pump (e.g., turn the pump on or off) based on measurements made from one or more sensors. For example, one sensor may be attached to a cell culture chamber. That sensor may measure, for example, glucose levels inside the media within the cell culture chamber. When the glucose levels fall below a pre-determined threshold, the processor may trigger the pump to replace the media in the cell culture chamber.

In some embodiments, the processor is configured to receive and execute instructions for culturing a cell type. In other instances, the processor may be configured to receive and execute instructions for transducing T cells.

In some embodiments, the substrate is configured to receive cell culture chambers of different sizes and/or shapes. This configuration is advantageous because it allows the system to be customized to culture different quantities of cells, or different cell types, depending on the particular needs of the user. The system may further include a plurality of pumps. For example, the system may include a separate pump for each cell culture chamber included within the system allowing for cells within each cell culture chamber to be separately cultured.

In some embodiments, the system further includes a plurality of tubes that fluidically connect from a first fluid reservoir on the first shelf to the plurality of pumps, from the plurality of pumps to a plurality of cell culture chambers, and from the plurality of cell culture chambers to a second fluid reservoir on the second shelf. Preferably, the system is dimensioned for insertion into an incubator.

In a related aspect, this disclosure provides a method for the sterile culture of cells. The method includes providing a cell culture system comprising a plurality of shelves stacked with a first shelf on top of a second shelf, each of the first and second shelves configured to receive a fluid reservoir; at least one pump; a processor operably coupled to the at least one pump; and a substrate sized and configured to hold a plurality of cell culture chambers at a same time. The method further includes loading a first fluid reservoir onto the first shelf, loading a second fluid reservoir onto the second shelf, loading a first cell culture chamber and a second cell culture chamber onto the substrate, connecting the fluid and second fluid reservoirs, the at least one pump, and the first and second cell culture chambers, with tubing; and operating the system to culture cells inside the first and second cell culture chambers.

In some embodiments, the first and the second cell culture chambers includes different sizes or shapes. In some embodiments, the system includes at least one sensor. In some embodiments, the processor is connected to at least one sensor and is configured to operate the pump based on a characteristic measured by the sensor.

DETAILED DESCRIPTION

The cell culture systems of the present invention significantly improve immunotherapeutic product manufacturing, providing flow-based immunotherapeutic production technology with an unparalleled degree of consistency, quality, safety, economy, scalability, flexibility, and portability. In general, cells are grown in single-use cell culture chambers, sometimes referred to as cartridges, which are perfused at low flow rates to achieve high expansion without the need for filters. The system supports one or more cell culture chambers to be fluidically coupled to one another for carrying out the processing of a patient's cellular material to generate an immunotherapeutic product, as described herein. It is to be understood that the bioreactors are provided in a closed environment in certain embodiments. Scale-up of this example embodiment will be within the knowledge of the skilled artisan by adding modules (e.g., biological reactors) to allow for serial and/or parallel processing. The skilled artisan will also appreciate that different or alternative arrangements may be desired based on the product to be produced.

Figure 1:
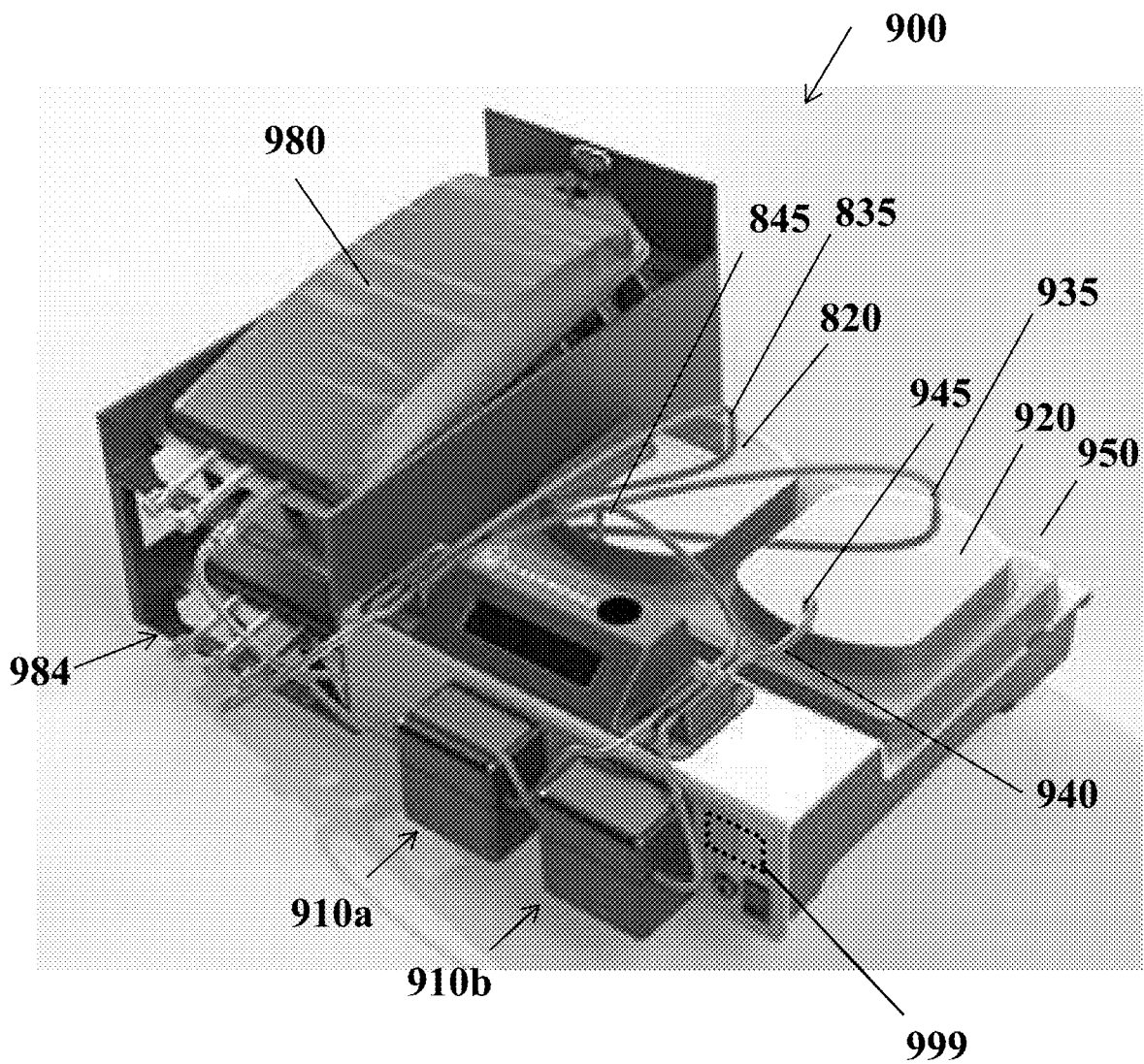
FIG. 1 shows an example of a multi-bioreactor system.

FIG. 1 shows an example of a multi-bioreactor system 900. The system 900 includes a first cell culture chamber 820 and a second cell culture chamber 920, which have inlets 845 and 945 connected to tubing 940 in fluid communication with a fluid reservoir 980. The cell culture chambers have outlets 835 and 935 in fluid communication with waste reservoir 984. Pumps 910*a* and 910*b* facilitation pumping of fluid from the fluid reservoir 980 to the cell culture chambers 820 and 920. The pumps are controlled by processor 999 in order to perform the functions described herein.

Figure 2:
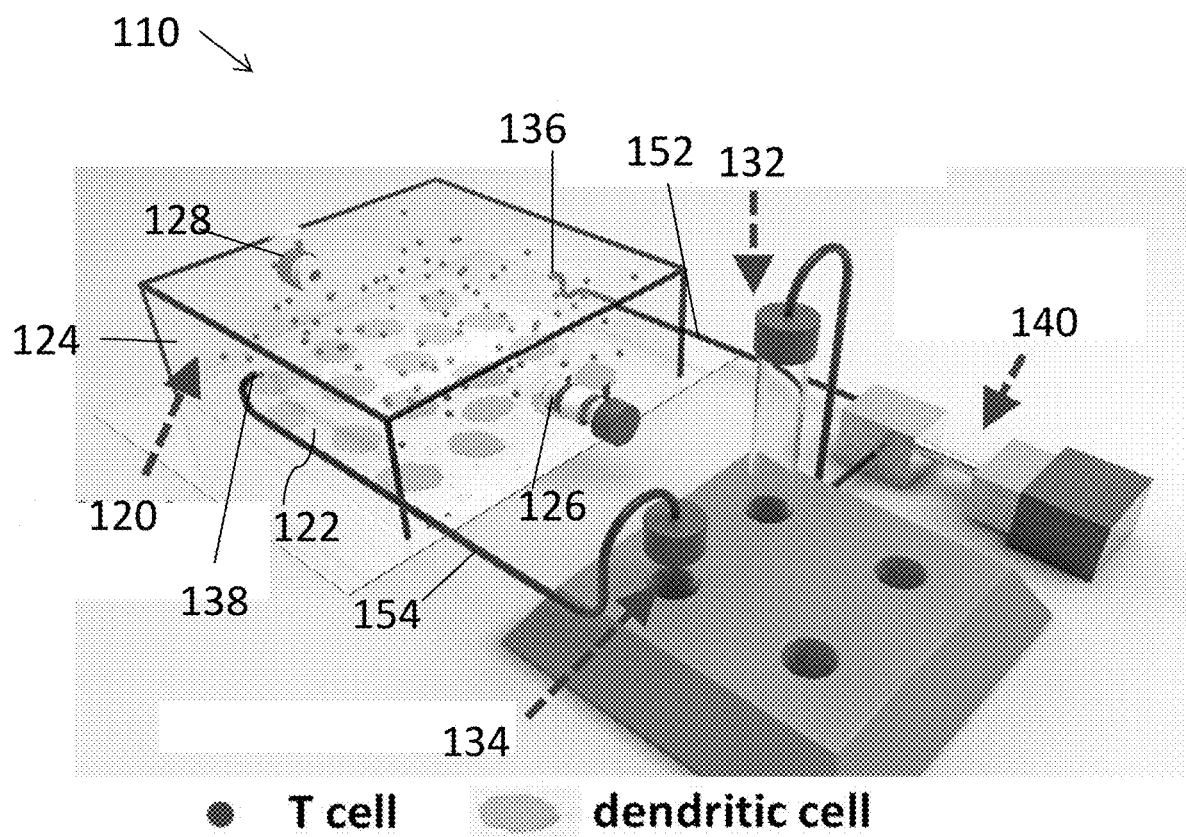
FIG. 2 shows an embodiment of a biological reactor.

Another embodiment of a biological reactor 110 is shown in FIG. 2, which provides a more detailed schematic view of the parts of the cell culture chamber 120. It is important to note that the cell culture platform described herein is configured to allow cell culture chambers of different volumes, shapes, and physical characteristics to be used. The chamber shown in FIG. 2 is exemplary only, and other embodiments will be apparent to the skilled artisan. As shown in FIG. 2, the cell culture chamber 120 includes a bottom surface 122 and at least one additional surface 124. The bottom surface 122 is comprised of a first material to which cells adhere. In some embodiments the at least one additional surface 124 is comprised of a second material that is gas permeable. In other embodiments, which will be described in greater detail below, the entire cell culture chamber 120, including the surface 124, is made of the first material which gas-impermeable. The cell culture chamber also comprises one or more inlets 126, 136 and one or more outlets 128, 138. In certain embodiments, the biological reactor also includes at least one perfusion fluid reservoir 132, at least one waste fluid reservoir 134, at least one pump 140 for moving perfusion fluid through the chamber 120, as well as associated inlets 136 and outlets 138 for transporting fluid to and from the reservoirs 132, 134 and through the chamber 120.

With respect to the cell culture chamber 120, the first material can be any material which is biocompatible and to which antigen-presenting cells (APCs) or their precursors, such as dendritic cells (DCs) or monocytes, respectively, will adhere. During the T-cell stimulation and expansion process that occurs in the cell culture chamber 120, mature APCs will develop and preferably adhere to the bottom surface 122, whereas the T cells remain in the supernatant above the bottom surface, making it easier to separately obtain the expanded T cells.

In one example embodiment, the first material comprises polystyrene. One benefit of using polystyrene for the bottom surface where culturing will occur is a useful role that this material plays in the process of generating dendritic cells from PBMCs. Specifically, polystyrene surfaces can be used to enrich monocytes from a heterogeneous suspension of PBMCs. This is a first step in the culture process utilized to generate DCs by differentiation of monocytes via culture in medium containing, for example, IL4 and GM-CSF. The use of the same polystyrene surface for dendritic cell production all the way through one cycle of T cell stimulation is tremendously valuable from a bioprocess standpoint as it eliminates a large number of transfer steps that would otherwise be necessary, thereby allowing for a closed system for DC-stimulated therapeutic T cell manufacturing.

The bottom surface can have a surface area comparable to conventional well plates, such as 6- and 24-well plates (9.5 cm$^2$ and 3.8 cm$^2$, respectively). It is also to be understood that the surface area can be smaller or even much larger than conventional well plates (e.g., having surface areas comparable to standard cell culture dishes and flasks), such as having a surface area between about 2.0 cm$^2$ and about 200 cm$^2$, for example, about 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 25.0, 30.0, 35.0, 40.0, 45.0, 50.0, 55.0, 60.0, 65.0, 70.0, 75.0, 100.0, 125.0, 150.0, 175.0, and 200.0 cm$^2$, and any surface area in between.

The at least one additional surface 124 can comprise any configuration, such as one or more side walls and a top wall. In one embodiment, as shown in FIG. 2, the side walls can be arranged at 90 degree angles with respect to one another, such that a box shape is formed in conjunction with the bottom surface 122. In another embodiment, the at least one additional surface 124 forms a curved side wall, such that the chamber 120 or a cross-section thereof forms a cylinder, elliptic cylinder, cone, dome-like shape, or triangular shape. It is to be understood that the above example configurations are non-limiting and that the at least one additional surface can have other configurations not provided in the aforementioned example configurations.

Figure 3:
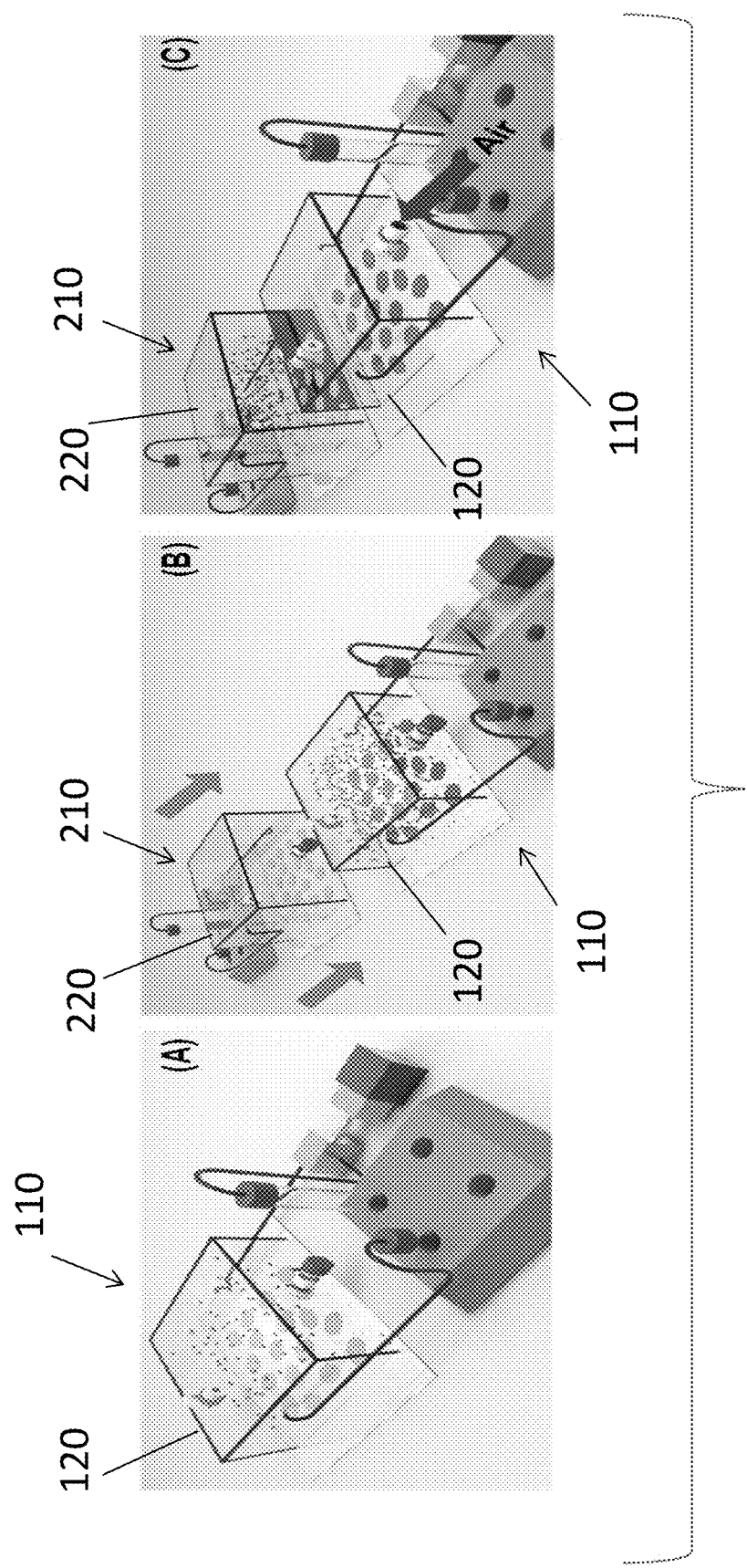
FIG. 3 shows a multi-bioreactor system.

An example configuration of a multi-bioreactor system can be found in FIG. 3, with additional detail regarding the processes carried out using this configuration provided below. As shown in FIG. 3, panel B, in the event that a second bioreactor 210 is involved, the second cell culture chamber 220 is positioned to connect with the first cell culture 120 chamber via the outlet of the first chamber and the inlet of the second chamber. The connection is preferably a sterile connection. The connection allows for the injection of sterile air into the first cell culture chamber 120 to transfer the supernatant containing the expanded T cells into the second cell culture chamber 220. Alternative techniques known in the art of fluid flow may be employed to transfer the supernatant from the first cell culture chamber 120 to the second cell culture chamber 220. As also shown, each bioreactor includes its own fluid and waste collection reservoirs, pumps, and associated tubing. However, it is to be understood that the reservoirs and pumps can be shared between bioreactors.

The system is configured to be able to perfuse the cells in the cell culture chamber with medium, which is required for various methods of cell culture described herein. Perfusion ensures uniform nutrient and cytokine supply to the cellular mixture along with sufficient gas exchange and waste removal to assist with the formation of the cell-based immunotherapeutic product. Maintaining consistent local concentration profile of medium and cytokines ensures greater yields and the potential ability to speed up the process of monocyte differentiation to DCs compared to prior art plate-based protocols. However, the combination of adherent (DC) and non-adherent (T cell) types, along with the high sensitivity of DCs to mechanical forces poses challenges to the stimulation and expansion of antigen-specific T cells, especially with respect to the flow of fluid through the cell culture chamber. Thus, in those embodiments in which medium and cytokines are provided via perfusion, systems of the present invention must be able to supply cells with nutrients and cytokines without removing cells from the bioreactor while also taking into account the shear sensitivity of certain antigen-presenting cells, such as DCs. Systems and methods of the invention aim to optimize retention of autocrine/paracrine signals favoring T cell proliferation while refreshing growth factors and maintaining minimal physical stimulation of DCs. In order to account for this, both the direction and the rate of perfusion flow through the cell culture chamber must be taken into consideration.

In certain aspects, the fluid flow rate is maintained below the sedimentation rate of the antigen-presenting cells. As such, the antigen-presenting cells will remain within the culture chamber because of their mass. In other words, the antigen-presenting cells will sink toward the bottom of the cell culture chamber and therefore remain in the cell culture chamber.

A flow rate that is lower than the sedimentation rate can be calculated according to Equation 1:

$$v\_max = [(\psi d\_p)]^2/150 \, \mu g(p\_cell - p\_liquid) e^3/(1-e)$$

where v_max is the liquid velocity beyond which cells will be lifted upwards, ψ is shape factor of cells (ratio of surface area of the cells to surface area of a sphere of equal volume; note that cells are not perfectly spherical and this factor is expected to be below 1), d_p is a diameter of a spherical particle of volume equal to that of a cell, µ is viscosity of liquid containing cells, g is the gravitational constant p_cell is the density of cells, p_liquid is a density of liquid containing cells, and e is a fraction of the volume of interest that is not occupied by cells.

In the methods described below that involve perfusion of medium, it should be understood that perfusion may be performed continuously during culturing or it can occur at specific points in time over the time period in which the cells are cultured in any one cell culture chamber, such as, for example, 1, 2, 3, 4, 5, 6, 7, 8, 9, 10, or more times each day or week. Continuous perfusion helps to maintain a near constant culture volume throughout the process. Likewise, cytokines can be infused at one or more points during culturing, such as, for example, 1, 2, 3, 4, 5, 6, 7, 8, 9, 10, or more times, or continuously. In those embodiments, the continuous perfusion helps maintain a consistent local concentration profile of cytokines, which can help to ensure greater yields and has the ability to increase the speed at which T cells are stimulated and expanded compared to static cell culture methods.

Perfusion parameters can be varied at any time during a culture cycle. Example parameters include, but are not limited to, the median flow rate, cytokine concentration, and duration of culture cycle. Each of these parameters may have an impact on the efficacy of T-stimulation. For example, in recent work designing culture chambers for monocyte-diffusion to DCs, as described in International Patent Application Nos. PCT/US2016/040042 and PCT/US2016/60701, it has been determined that medium perfusion rates corresponding to wall shear stress levels of 0.1 dyn/cm2 are capable of producing DCs that are phenotypically identical to those generated using conventional 6- or 24-well plate-based protocols. As such, by measuring the one or more of the phenotypic and functional measures described above during the culture cycle, the effect of one or more perfusion parameters on efficacy can be monitored, allowing for appropriate adjustments.

To facilitate perfusion, the system includes one or more pumps 140. The pumps can be operably coupled to the cell culture chamber 120 for perfusing perfusion medium into the cell culture chamber. The bioreactors 110 can also include one or more fluid reservoirs 132. The fluid reservoirs 132 are in fluidic communication with the cell culture chamber 110 and can be operably coupled to one or more pumps 140. One or more tubes for connecting the fluid reservoirs to the pumps and cell culture chamber are also provided. In certain aspects, the one or more pumps are configured for pumping fluid from the fluid reservoir, through the cell culture chamber, and into the waste collection reservoir. In the example embodiment shown in FIG. 2, fluid moves from the fluid reservoir 132, through tubing 152 to the pump 140 and into the cell culture chamber 120 via inlet 136, back out of the cell culture chamber 120 via outlet 138, through tubing 154, and into the waste collection reservoir 134.

In certain embodiments, the fluid reservoir and/or waste collection reservoir can each be provided as one or more sealed bags or containers fluidically coupled to the chamber. Each reservoir contains an inlet port and an outlet port, or an outlet port and a vent fluidically coupled to the inlet of one or more cell culture chambers. In some embodiments, Luer connectors and silicone gaskets cut to fit around the Luer connectors can be used to prevent leakage through either or both of the inlet or outlet. In some embodiments, the sealed reservoirs can be connected to the cell culture chamber using a sterile tube welding device that creates a fluidic connection without exposing either vessel to the outside environment and maintaining sterility. As will be discussed in greater detail below, this allows methods of the invention to be performed in a closed system.

Due to the small size and portability of the disclosed cell culture systems, they can be easily used in conjunction with a tube welding device. Systems of the invention can be easily lifted and carried into proximity with a tube welder in order to make the necessary sterile connections. The size and configuration of the cell culture systems also makes them compatible with standard incubators. The cell culture systems are sized and configured to fit on a single shelf inside a conventional incubator, such that the disclosed processes can be carried out therein. Multiple instruments can fit in a single incubator, depending on the configuration. Conditions within the incubator include sustained temperatures of 37° C. and 95-100% humidity. Thus, the materials chosen must have the integrity to withstand these conditions, given that the materials (including fluids and biologics) tend to expand under such conditions. Furthermore, in some circumstances, conditions within the incubator remain stable, and automated recording of the temperature is possible to have knowledge of temperature fluctuations to correlate with any aberrations in the reactions performed in the incubator.

Accordingly, any supply of power should not change the environment within the incubator. For example, certain pumps generate heat. Accordingly, in one embodiment, the pumps are housed separately from the biological reactors, but are still in fluidic and operable communications with the reactors. In another embodiment, the pumps are directly attached to the biological reactors and located within the incubator, but are heat free or are operably connected to a heat sink and/or a fan to dissipate the heat. In another embodiment, the pumps run on a duty cycle to reduce the amount of heat generated. Regardless of the configuration, the pumps are operably coupled to the biological reactors, and, in turn, the cell culture chambers. In some embodiments the system also includes a heater for controlling the temperature of the cell culture reservoir and optionally the fluid reservoir. In such a configuration, no incubator is required, and the system can operate autonomously, with only a source of electrical power. If the system lacks a heater, it can be operated inside of a cell culture incubator.

Additional details regarding perfusion-based automated cell culture systems, such as small scale culture system for endothelial cell culture with on-board reagent storage and perfusion enabled by an on-board disposable peristaltic pump and a larger scale culture system for dendritic cell generation from monocytes using chambers with polystyrene bottom surfaces, can be found in international patent publications WO 2017/004169; WO 2017/079674; and WO 2018/005521; as well as U.S. patent application Ser. No. 16/539,916; each of which is incorporated herein by reference in their entirety.

Systems, or devices, of the invention are modular and capable of fluidic connection to other similar devices in series (i.e., with fluid flowing from one device into another) and/or in parallel, and may also be so configured as to physically stack with one another or be capable of physical arrangement within a related device such as an incubator. The modular design of the system specifically allows for modules to be flexibly switched in and out depending on a desired process to be included within the system.

Fluidic devices of the invention, including the biological reactors comprising cell culture chambers, can be provided in either a microfluidic embodiment (i.e., wherein one or more channels or chambers therein has a dimension in the range of from about 1 μm to about 999 μm) or a macrofluidic embodiment (wherein all of the channels or chambers therein have dimensions of about 1 mm or more), or both.

The fluidic devices can further include additional fluid channels or compartments, gaskets or seals, mixing zones, valves, pumps, vents, channels for pressurized gas, electrical conductors, reagents, ports, and tubing as required by a particular design. They also may contain one or more control modules, transmitters, receivers, processors, memory chips, batteries, displays, buttons, controls, motors, pneumatic actuators, antennas, electrical connectors, and the like. The devices preferably contain only materials that are nontoxic to mammalian cells and that are compatible with sterilization by the use of alcohol and/or heat or other means, such as exposure to gamma radiation or ethylene oxide gas.

The materials of equipment are chosen with the appropriate chemical compatibility under different temperature and pressure rating specific to each process. Additionally, the choice of pumps implemented in the device, such as syringe, peristaltic, pressure, and rotary pump, ranges from a nL to a mL in flow rates and 10 to 10,000 psi in pressure depending on the flow and pressure requirements for the different functions.

Systems of the invention can also include one or more sample solution reservoirs or well or other apparatus for introducing a sample to the device, at various inlets of the modules, which are in fluid communication with an inlet channel. Reservoirs and wells used for loading one or more samples onto the fluidic device of the present invention includes but are not limited to, syringes, cartridges, vials, Eppendorf tubes and cell culture materials (e.g., 96 well plates).

Where useful, surfaces of the devices can be made more hydrophilic, such as by exposure to a plasma, or can be coated with one or more gels, chemical functionalization coatings, proteins, antibodies, proteoglycans, glycosaminoglycans, cytokines, or cells. Fluidic devices of the invention are preferably devoid of fluid leaks under operating conditions and capable of sterile operation over a period of days to weeks. Fluidic devices of the invention also include a sampling mechanism that allows fluid to be removed from the system for testing without introducing new material or contaminants to the system.

In certain aspects, at least part of the cell culture system comprises disposable components, some or all of which can be housed within a non-disposable frame. In other aspects, all components of the system are disposable. Furthermore, in some embodiments, the cell culture system includes a sample tracking component for tracking and documenting patient material.

At least one step, and sometimes a plurality or all steps, during the manufacturing process are monitored for product characteristics (e.g., purity and polymorphic forms) using a variety of inline process analytical tools (PAT) or miniaturized micro-total analysis system (micro-TAS).

As described above, the cell culture systems of the present invention are capable of controlling the direction and flow of fluids and entities within the system. Systems of the invention can use pressure drive flow control, e.g., utilizing valves and pumps, to manipulate the flow of cells, reagents, etc. in one or more directions and/or into one or more channels of a fluidic device. However, other methods may also be used, alone or in combination with pumps and valves, such as electro-osmotic flow control, electrophoresis and dielectrophoresis (Fulwyer, Science 156, 910 (1974); Li and Harrison, Analytical Chemistry 69, 1564 (1997); Fiedler, et al. Analytical Chemistry 70, 1909-1915 (1998); U.S. Pat. No. 5,656,155).

Systems of the invention can also include or be operably coupled to one or more control systems for controlling the movement of fluid through the system; monitoring and controlling various parameters, such as temperature, within the systems; as well as detecting the presence of cell-based immunotherapeutic products, quantity of product (directly or indirectly), conversion rate, etc. The system may also be equipped with numerous classes of software, such as an advanced real-time process monitoring and control process, allowing for feedback control, as well as processes that allow integration and scale-up given reaction and purification results obtained using the system.

In certain embodiments, the system includes a combination of micro-, or macrofluidic modules and tubing that are interchangeable in terms of channel dimensions, flow geometry, and inter-connections between the different modules of the device. Each module and tubing may be designed for a specific function. In one embodiment, all of the modules within the system are designed for cell culturing and T-cell stimulation. In other embodiments, the modules with the system are designed for different functions, such as tissue processing, dendritic cell generation, cell culturing, concentration, and/or purification, all integrated for the continuous manufacturing of an immunotherapeutic product. Both homogenous and heterogeneous processes are considered which are suitable for flow application. These processes are designed and optimized with respect to the starting materials and operating conditions, such as temperature, pressure and flow rates so as to not readily clog the system during the flow process.

Gas-Impermeable Cell Culture Chambers

In some embodiments, the cell culture chambers of the disclosed system are made of a gas-impermeable material. The gas-impermeable material is biocompatible and is a material to which dendritic cells will adhere. In one example embodiment, the gas-impermeable material comprises polystyrene, which as described above is useful for enriching monocytes from a heterogeneous suspension of PBMCs. The entire cell culture chamber being made of the gas-impermeable material offers a larger surface area to which cells can adhere and increases the sterility of the system.

A gas-impermeable cell culture chamber can be substantially the same as the chamber 120 shown in FIG. 2 and can have any volume, shape, size, and physical characteristic described above, with the exception that the additional surface 124 and all other surfaces of the chamber 120 are made of the same material as the bottom surface 122. In some embodiments, the top, bottom, and all side walls of the chamber 120 are gas-impermeable. The bottom surface of the gas-impermeable cell culture chamber can have a surface area comparable to conventional well plates, such as 6- and 24-well plates (9.5 $cm^2$ and 3.8 $cm^2$, respectively). It is also to be understood that the surface area can be smaller or even much larger than conventional well plates (e.g., having surface areas comparable to standard cell culture dishes and flasks), such as having a surface area between about 2.0 $cm^2$ and about 200 $cm^2$, for example, about 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 25.0, 30.0, 35.0, 40.0, 45.0, 50.0, 55.0, 60.0, 65.0, 70.0, 75.0, 100.0, 125.0, 150.0, 175.0, and 200.0 $cm^2$, and any surface area in between.

Certain modifications need to be made to the system described above when the chamber is not permeable to gas. For example, in such embodiments where gas does not flow through one of the surfaces of the cell culture chamber, the gas exchange between cells and the medium must be facilitated in another way. The cell culture chamber comprises one or more inlets 126 and 136 and one or more outlets 128 and 138. The inlet and outlet openings can be fluidically coupled to tubing, which is sealed with the respective opening. The inlets and outlets are thereby connectable to a perfusion fluid reservoir and a waste fluid reservoir with corresponding pumps for moving perfusion fluid through the chamber. The inlets and outlets can be located in any surface of the chamber. In some embodiments, they are located in the top of the chamber. The tubing is preferably high-permeability tubing, In order to effectuate gas exchange, the medium can exchange gas prior to entry into the chamber and after leaving the chamber through the high-permeability tubing. Gas is therefore effectively brought into the chamber through the one or more inlets and removed through the one or more outlets. The inlets or the tubes connected thereto can include a filter such as a 0.2 micron filter, for filtering liquid or air entering the cell culture chamber.

Gas flow is affected by perfusion rates, the parameters of which can be controlled as described above. By exchanging gas via the high permeability tubing, the system maintains the ability to achieve the required levels of gas exchange without requiring the chamber to be gas permeable. Methods of cell culture can be performed in a completely gas-impermeable chamber, with inlets 126 and 136 and outlets 128 and 138 for perfusion and gas flow. In methods embodiments, the gas-impermeable cell culture chambers can be used to culture cells by loading cells into the chamber and perfusing them by flowing cell culture medium in and out of the chamber via the inlets and outlets. The perfusion flow provides nutrients as well as gas exchange to the cell culture. Because flow through the chamber is laminar, some methods may require additional shaking, such as for cell harvesting. However, given the size and configuration of the disclosed systems, the entire system can be placed on an orbital shaker as needed.

Another advantage of gas-impermeable embodiments is that they are easier to manufacture because they have fewer different parts and materials. They can be made as large or small as needed. The gas impermeable chamber can be integrally formed or it can be formed from multiple parts. For example, it can be formed out of a single piece of material by traditional manufacturing processes or additive manufacturing processes such as 3D printing. In embodiments, a plurality of members, each made of the gas-impermeable material, are joined together using methods known in the art, such as mechanical fastening, adhesive and solvent bonding, and welding, such as ultrasonic welding.

Interchangeability of Cell Culture Chambers

Cell culture systems of the present invention are configured to be able to connect with cell culture chambers of various sizes and shapes. The cell culture system can include a fluid reservoir, a waste reservoir, and one or more pumps for controlling fluid flow to and from the reservoirs. The cell culture system also has an area configured to receive one or more cell culture chambers of different shapes and sizes. One or more tubes fluidically connect the fluid reservoir, the cell culture chambers, and the waste reservoir. The pumps are configured to move fluid through the tubes.

Different cell culture chamber sizes can be used for different purposes, or in combination with each other. The size can be selected based on the desired cell output, or different proportions of reagents needed. For example, small cartridge sizes can be useful for research, pre-clinical uses, or process development. Large cartridges are a higher capacity version with the same architecture.

The height of the one or more cell culture chambers can vary. For example, and not limitation, an example range of cell culture chamber heights includes heights of anywhere from 0.5 mm to 100 mm, such as 0.5, 1.0, 2.0, 3.0, 4.0, 5.0, 6.0, 7.0, 8.0, 9.0, 10.0, 15.0, 20.0, 25.0, 30.0, 35.0, 40.0, 45.0, 50.0, 55.0, 60.0, 65.0, 70.0, 75.0, 80.0, 85.0, 90.0, 95.0, 100.0 mm, or more, or any height therebetween. In certain embodiments, the heights of the chamber can be comparable to liquid heights in cultures that are typically performed in 6- and 24-well plates, such as between 2 and 6 mm, with a volume capacity of about 0.8 mL to 6 mL. In other embodiments, the cell culture chambers will be of larger size, such as between 10 mm and 50 mm, with a culture surface of about 50 $cm^2$. In some embodiments the cell culture chamber has a volume capacity of between about 1 mL and about 100 mL, and may be approximately 5, 10, 20, 25, 30, 40, 50, 60, 70, 80, or 90 mL, or anywhere in between. In other embodiments the cell culture chamber has a volume capacity of between about 100 mL and about 1,000 mL, for example 100, 200, 300, 400, 500, 600, 700, 800, 900, or 1,000 mL. In a particular embodiment a cell culture chamber has a capacity of 210 mL.

The interchangeability of cartridges with the present invention allows scaling up during a cell growth procedure using the same system. This avoids the need to switch to a different cell culture system in order to continue growing cells. For example, to manufacture a batch size of about 2 billion cells, the system can start with a small cartridge with a capacity of about 25 mL, and then scale up to a large cartridge with a capacity of about 210 mL. This interchangeability means that more parts of the process can be done on the same system, from activation through fill and finish. Depending on the needs of a particular protocol, the system is operable with, for example, two large (approximately 210 mL) cell culture chambers, two small (approximately 25 mL) cell culture chambers, or one of each. Since each inlet and outlet can be connected to any size chamber, the system is capable of scaling up or scaling down as needed.

With reference once again to FIG. 1, the system 900 includes a platform 950 configured to support one or more cell culture chambers 820 and 920. Regardless of shape or size, the cell culture chambers can be connected via tubes 940. In this way, cell culture chambers of different shapes and sizes are compatible with the system. The cell culture chambers can be arranged in different configurations on the platform, such as positioned side-by-side or stacked. In embodiments, the tubes 940 are integrally formed with the chamber. The tube and the chamber body can be joined together using the same manufacturing methods discussed above. In one embodiment, the cell culture chamber is manufactured with at least a portion of the material in the side and/or top walls cut out to allow for the formation of the one or more inlets or outlets. In an example arrangement, a tube can be separately inserted into the openings to form a seal with the vessel. It is to be understood that the aforementioned configurations are only examples and that other configurations for joining the chamber and one or more tubes are also contemplated embodiments of the present invention.

Interchangeability is facilitated in part by using sterile tube connections to couple the various vessels and chambers of the system. The sterile tubes are preferably connected using a sterile tube welder. Generally a sterile tube welder is a device that can receive two tubes, secure them in place, and then cut them with a hot blade, realigns them so that the first tube and second tube are aligned, and melts the two cut ends together when the blade is retracted. Sterile tube welders for use with the present invention can be any commercially available sterile tube welder, including SCD®

IIB from Terumo BCT, Inc. (Lakewood, CO); the Vante® 3690 from Vante BioPharm (Tucson, AZ); and the TCD® from Genesis BPS™ (Ramsey, NJ).

As will be described in greater detail below, in certain embodiments the system is functionally closed. The closed system is maintained by all of the transfers being done using sterile tube welding. For example, cells may be stored in a sterile bag, which is then connected to a sterile cell culture chamber. The cells can be flowed into the cell culture chamber while maintaining sterility. The tube connectivity allows cell seeding, washing, and harvesting to all be done on the same device under sterile conditions. By using the sterile tube welder, one bag does not have to be disconnected before connecting another.

The above description focuses on the system components and various possible configurations. The following description focuses on certain processes that can be carried out using systems of the invention.

CAR-T and TCR Processes in a Closed System

Figure 4:
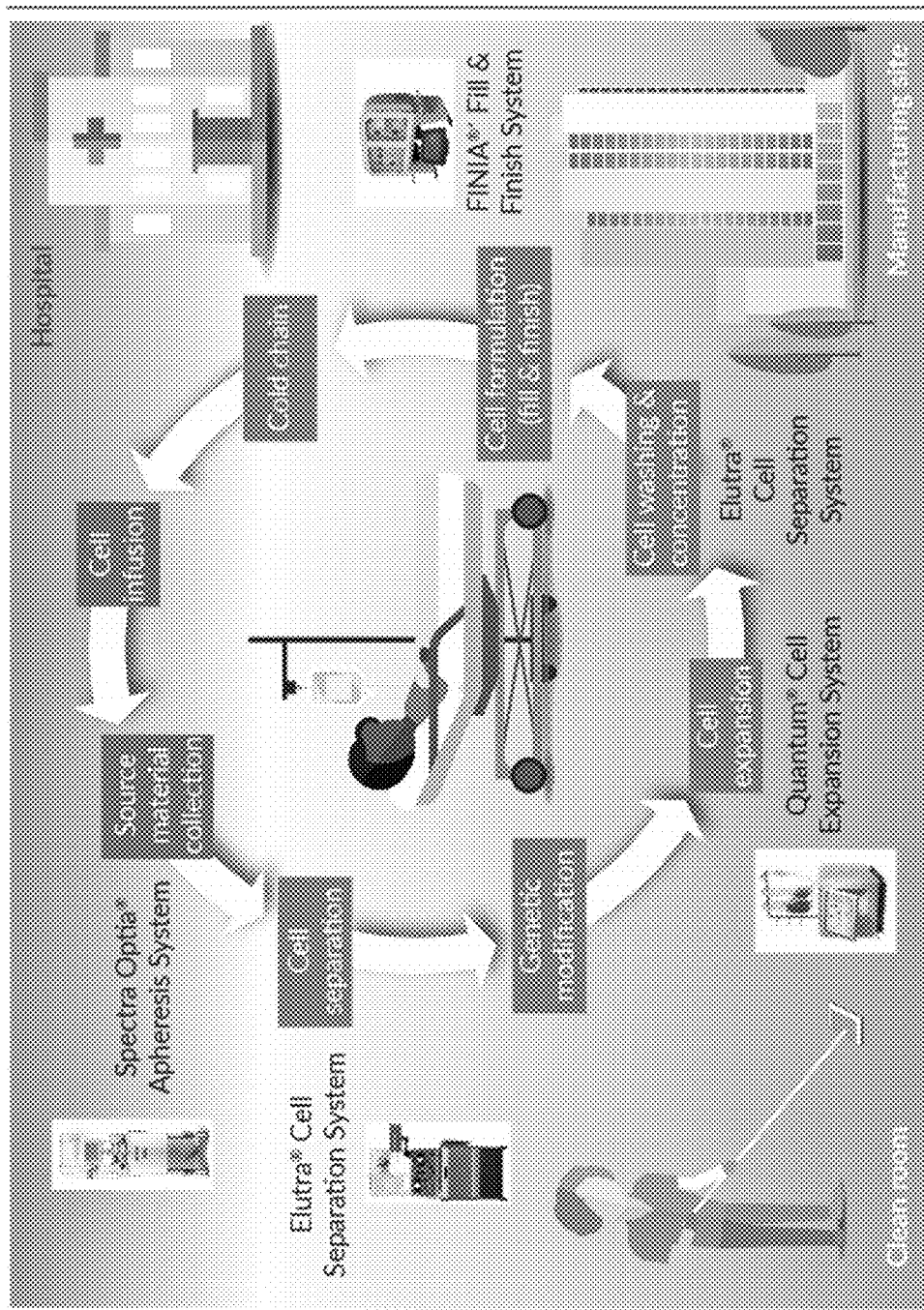
FIG. 4 shows a CAR-T/TCR workflow.

The cell culture systems described above are useful for methods of producing CAR-T and TCR transduced T cells. A visualization of a CAR-T/TCR workflow is shown in FIG. 4. The disclosed system can be used to perform several of the steps of the workflow in a closed system, including genetic modification, cell expansion, cell washing and concentration, and cell formulation. Prior known methods used in the industry producing CAR-T and TCR transduced T cells are not performed in a closed system. Commonly used polystyrene T flasks have to be opened and closed to perform transfers, and are therefore subject to potential contamination. The present invention uses closed and interchangeable cartridges made of solid polystyrene, which allows protocols designed for T flasks to be easily reformatted to be done on the disclosed sterile system.

In some embodiments, a method of the invention involves flowing cell culture medium into a culture chamber with T cells, and perfusing the T cells to transduce them with a transduction reagent such as an inactive virus expressing CAR or TCR, for example. The perfusion fluid may include an activation reagent to expand the cells. In some embodiments the transduction and/or activation reagents are pre-mixed with the cells, and in other embodiments they are from a separate sterile bag or vessel. The bags can be connected through sterile welding means as described above, and the reagents can be flowed into the bag by gravity or by a pump. In some embodiments, the cell culture chambers are filled completely with little or no headspace.

The cells are grown for up to about 3 days, during which time they are allowed to take on CAR, TCR, and are sustained by the perfusion medium. The cells form a sediment in the chamber and the perfusion rate is maintained low enough to prevent the cells from flowing out of the cartridge. The transduced cells are expanded in the culture chamber and then can be transferred to a larger culture chamber, which is connected via a sterile tube, for further expansion. Using methods of the invention a 7-day expansion in a small cartridge (25-mL volume) can yield about 500 million to one billion T cells, and a large cartridge (210-mL volume) can yield about one to three billion T cells.

The connection with the perfusion bag is detached and a harvest bag is attached. The cells are then drained into the harvest bag. In embodiments, a buffer bag can be connected by the same methods and used to perform one or more washes of the cells before they are removed into the harvest bag. The volume of liquid that the cells are in can be increased or decreased, by draining one liquid, adding another, and resuspending the cells in the new volume of liquid. In some embodiments, the system can be drained to remove built-up lactic acid. As the cell culture expands, lactic acids builds up and may not be removed fast enough through perfusion alone. A solution is to drain the medium to reduce the total volume (by perhaps 90-95%) without removing the cells, and then perfuse with fresh medium. In some embodiments, the medium can be replaced with a different cell culture medium or cryopreservation medium.

The cell culture chambers are connected in a closed system such that the entire method is performed in a closed environment without the need to expose the media to air by opening any of the vessels when transferring. As has been mentioned, all of the connections and disconnections of the method can be done with a sterile tube welder.

Unlike the prior art, the disclosed method of activation, transduction, and expansion are performed in a closed sterile system. With the interchangeability described above, a user can scale up to a batch of up to 10-20 billion expanded cells, all in a closed environment. In some embodiments, the methods may be used to prepare a batch for manufacturing on a larger bioreactor system. In conventional CAR-T manufacturing, batches of 10 billion or more cells are needed. The presently disclosed systems and methods can perform the upstream steps of activation, transduction, and initial expansion, prior to transferring 1 billion or more cells to a larger expansion system, such as XURI™ available from GE Healthcare (Chicago, IL). This capability makes the systems highly compatible with non-magnetic activation reagents.

Figure 5:
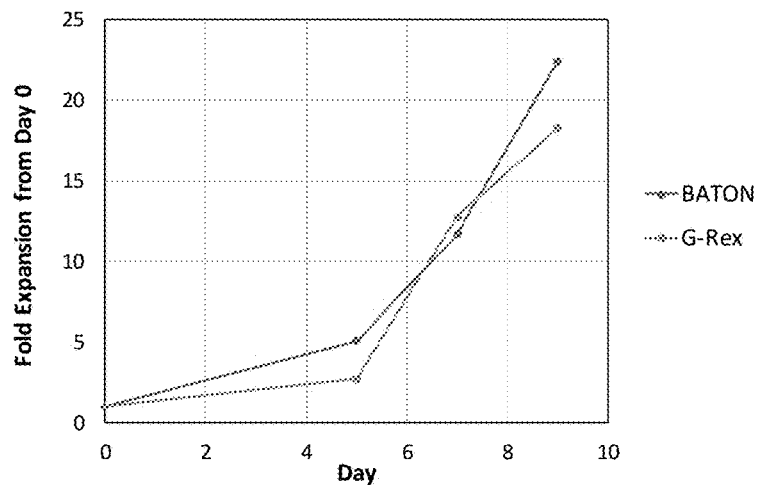
FIGS. 5-8 show comparisons of T cell expansion using different systems.
Figure 6:
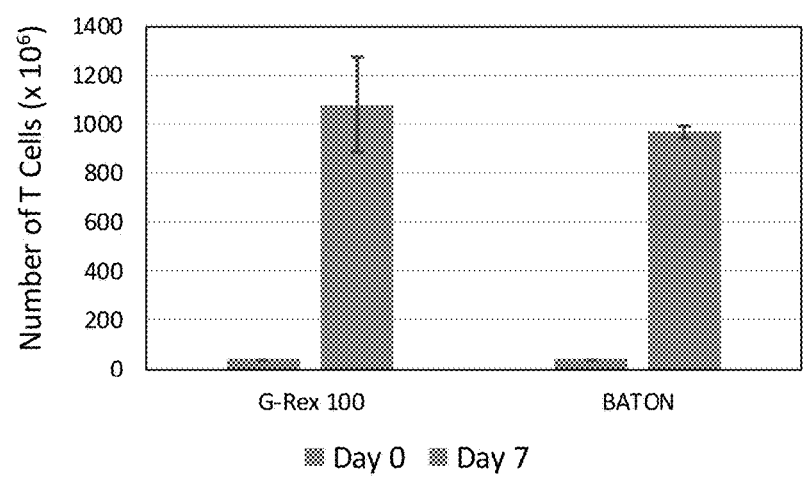

FIGS. 5-6 show an example of the comparison between a T cell expansion conducted with the presently disclosed system, known as BATON™ from Flaskworks, LLC (Boston, MA), and another commercially available T cell expansion platform G-REX® from WilsonWolf (St. Paul, MN). FIG. 5 shows a graph of the fold-expansion using BATON™ over 9 days with PBMCs stimulated with DYNABEADS® from Thermo Fisher (Waltham, MA) run in a 25 mL cartridge. The robust fold-expansion achieved with BATON™ is comparable to that of G-REX®.

Figure 7:
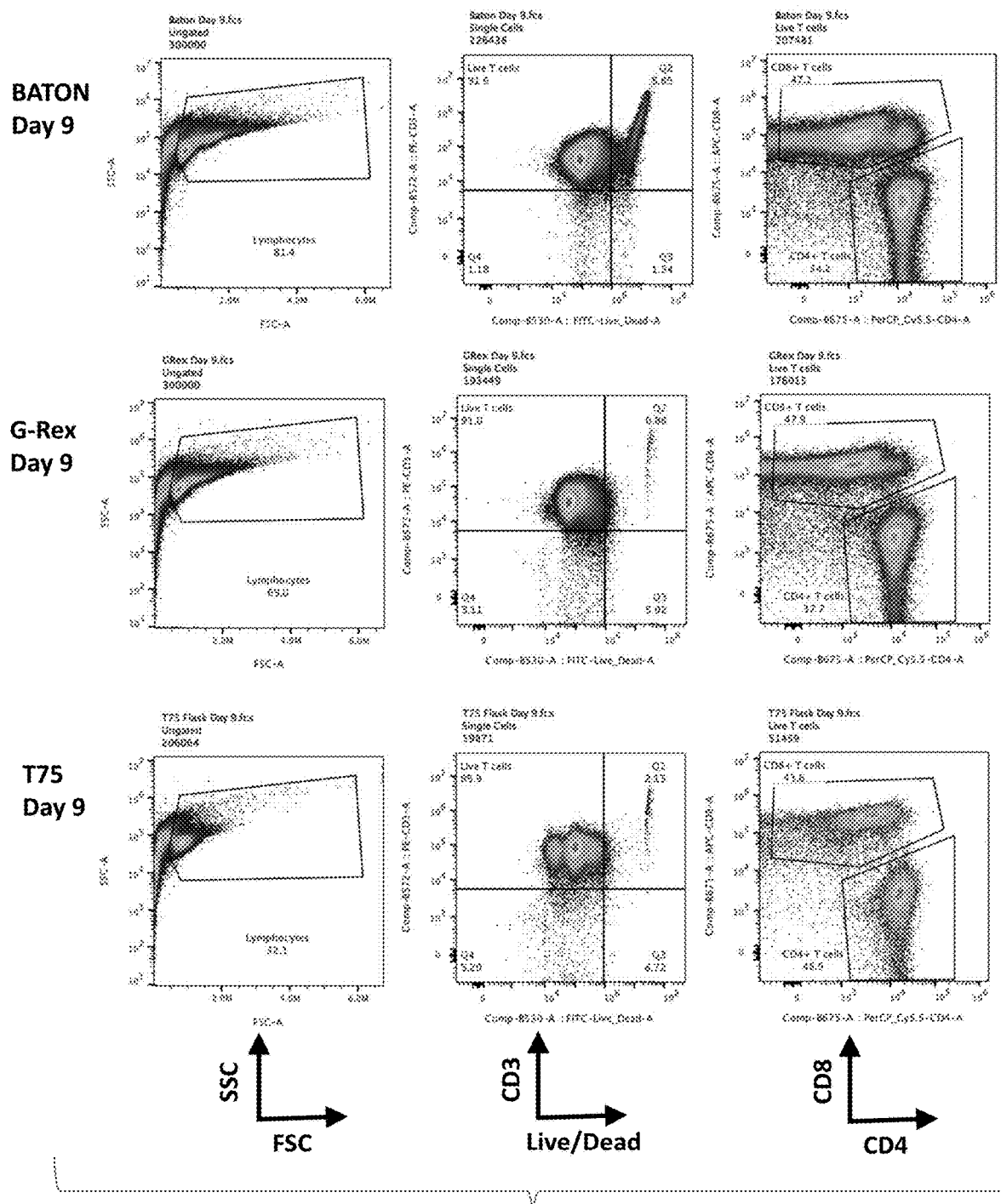

FIG. 6 shows the number of cells on day 0 and day 7, using both systems. With BATON™, approximately a billion cells were obtained from 40 million T cells in seven days in a 210 mL cartridge in accordance with the present disclosure. The phenotype is predominantly central memory. As further shown in FIG. 7, phenotypic profiles are comparable between BATON™ and G-REX®. The figure also compares T75 flasks available from Corning Inc. (Corning, NY). As shown, both BATON™ and G-REX® generated equivalent CD4/CD8 ratios for Day 9.

Figure 8:
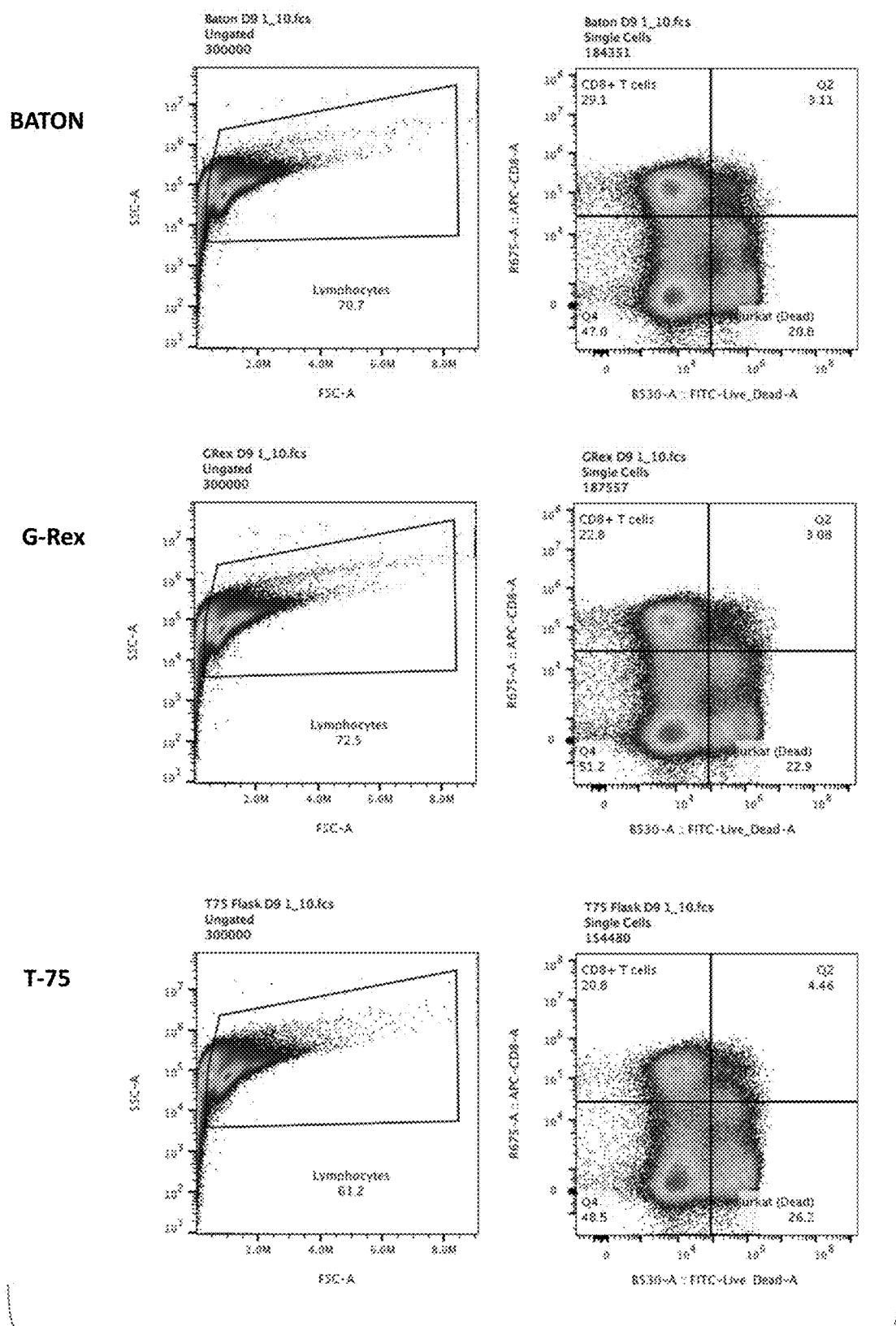

As shown in FIG. 8, the cytotoxicity of T cells produced with BATON™ is comparable to that of G-REX®. The effector cells were expanded for 9 days, and the target cells were Jurkat T cells. Cells were mixed at a 10:1 ratio of effector-to-target and incubated at 37° C. at 5% $CO_0$ for 24 hours. The medium was RPMI 1640 (ATCC)+15% FBS. The Day 5 and Day 7 cells from all three groups were comparable in cytotoxicity.

Neoantigen Process on a Closed System

The disclosed systems are also useful in a workflow for producing neoantigen-targeting T cells. This class of therapeutics involves the co-culture of antigen-presenting cells stimulated with libraries of tumor-specific peptides and autologous T cells. Manufacturing of neoantigen presenting cells is more complex than CAR-T. Unlike CAR/TCR, the present method can pursue a library of targets rather than just one. It requires certain capabilities provided by the presently disclosed systems which are not available from prior art systems.

The present system generates fresh dendritic cells from patient monocytes. The system also is configured to co-culture dendritic cells with patient PBMCs or T cells and deliver stimulated T cells. The system can perform multiple cycles of co-culture with freshly generated dendritic cells to avoid competing effects between different antigens. Parallel processing of dendritic cells and T cells to facilitate this process will be described in greater detail below. The typical dose sizes for neoantigen therapies are about 200 million T cells, which can be handled by the disclosed system in either a small (approximately 25 mL) or large (approximately 210 mL) cartridge.

Unlike prior art methods, systems of the invention facilitate all of the above in a closed environment. The method utilizes the interconnected cell culture chambers of the present system. Purified monocytes are introduced to one of the cell culture chambers, and purified T cells are introduced to the other. The monocytes are perfused with cell culture medium to produce dendritic cells, which are then contacted with antigen material comprising tumor-specific peptides. This produces mature dendritic cells presenting tumor-specific peptides. T cells are transferred into to chamber containing the mature dendritic cells to co-culture them with the T cells. Co-culturing produces neoantigen-targeting T cells. After one cycle of stimulation via co-culture, the T cells can be removed and optionally flowed into a second chamber containing freshly generated mature dendritic cells to perform a second co-culture. The second batch of dendritic cells can be produced asynchronously from the dendritic cells generated in the first chamber.

In embodiments, mature dendritic cells are generated in a first chamber and then T cells added to the first chamber and co-cultured. T cells from the first chamber are then moved to a second chamber where they are co-cultured with freshly generated dendritic cells that are stimulated with either the same or a different set of peptides. The expanded T cells can then be moved back to the first chamber where yet another batch of fresh mature dendritic cells stimulated with either the same or different set of peptides await.

The T cells can be transferred back and for the between two connected chambers any number of times as desired. This can be particularly useful for stimulating DCs with several different peptides. For example, if one has a library of 20 or so peptides with which the DCs need to be stimulated, attempting to stimulation the DCs with all peptides at once would result in insufficient stimulation because of competing effects between the peptides. Some peptides have greater effect and/or affinity than others. Performing the stimulation in stages, for example, stimulating a batch of DCs with five peptides in a first co-culture, and then stimulating the next batch of DCs with five different peptides in a second co-culture, and so on. In other embodiments, multiple stimulation cycles can be done with a single, small group of peptides. In nonlimiting embodiments, the T cells can be transferred 2, 3, 4, 5, 6, 7, 8, 9, 10, 15, 20, or 25 times. Each co-culture can involve DCs stimulated with the same or different peptides.

The entire method is performed within the closed system of the present disclosure, thereby maintaining sterility throughout the method. Like the other disclosed methods, the culture chamber connections can be achieved with sterile tubes that are connected with a tube welder. This maintains that sterility of the cell culture medium that is provided in a sterile vessel. In various embodiments, the T cells can be transferred between chambers on the same instrument or transferred between chambers on separate instruments.

After the co-culture is complete, fluid is drained from the chamber, and the neoantigen-targeting T cells can be washed with a buffer and resuspended in a cryopreservative and/or harvested in a harvest bag, which is also connected in a closed manner.

Figure 9:
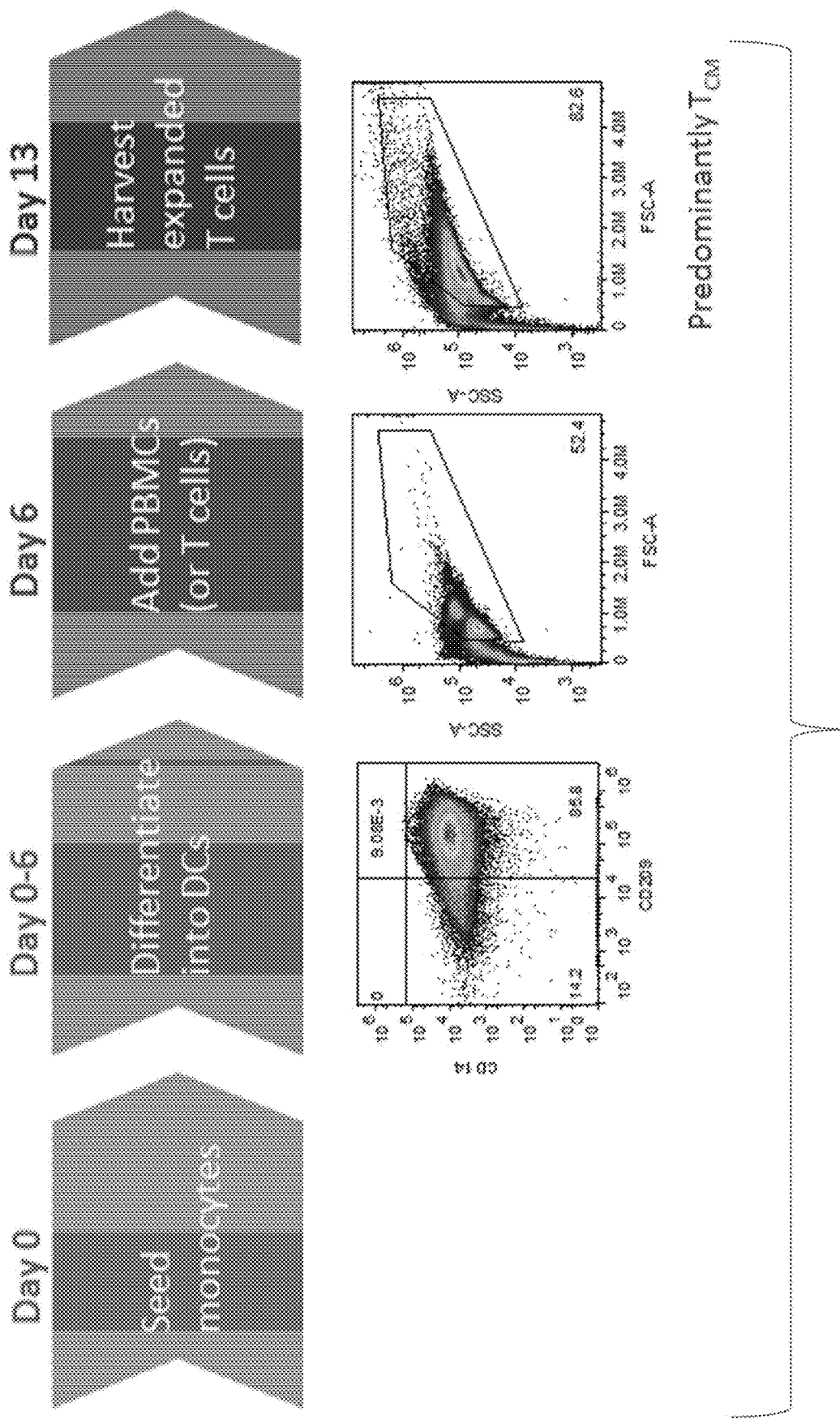
FIGS. 9-10 show a method for co-culturing freshly cultured dendritic cells and PBMCs or T cells, and results thereof.

FIG. 9 shows a schematic flowchart of a method for co-culturing freshly cultured dendritic cells and PBMCs or T cells on the closed system of the present invention. Using sterile welded connections, the disclosed cell culture system provides automated seeding, culture, and cell harvesting. As shown in the workflow, monocytes are seeded at day 0, and differentiate into dendritic cells over days 0-6. At day 6, allogeneic PBMCs or T cells are added. Dendritic cells enable T cell expansion from PBMCs. The expanded T cells are harvested on day 13.

Figure 10:
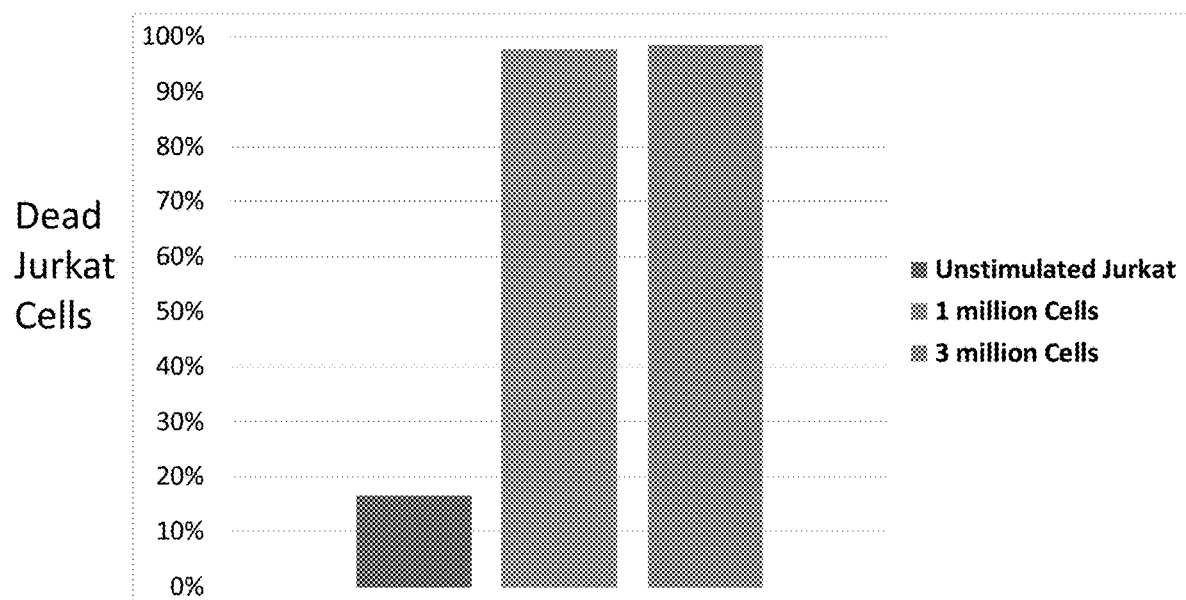

Expanded T cells produced with the disclosed methods show a robust cytotoxic ability. Results of an example performed using the workflow is shown in FIG. 10. The target ratio of CD 8+ T cells to Jurkat cells was 1:1, with experiments performed using 1-3 million harvested cells. Jurkat cells were stained with PKH67 prior to the assay. Cells were incubated for 1 day, and all cells were stained with CD3 and Annexin V post-assay. The resultant dead Jurkat cells are shown in FIG. 10.

Parallel Processing of Dendritic Cells and T Cells

The process for forming cell-based immunotherapeutic product requires co-culturing two types of cells. With the presently disclosed systems, these cells can be generated in parallel for more efficient generation of antigen-specific T cells. In brief, dendritic cells are produced from monocytes and matured by contact with antigen material, and T cells are activated and then co-cultured with the DCs. In prior art methods, this method would require several manual steps. The current system however can produce the two cell batches in parallel in a closed system. Using the systems disclosed herein, dendritic cells are produced in one chamber and, in parallel, T cells are stimulated in another connected chamber. Monocytes are perfused in a first chamber to produce DCs, which are contacted with antigen material to mature them. Activated T cells from another connected chamber are flowed into the first chamber to contact the DCs and further culture the T cells. Like in the other methods, the chambers are connected via a sterile tube, so that the method is performed in a substantially closed system. The T cells can be collected by flowing them into a collection vessel and/or transferred to a cryopreservation medium, while still in a closed system configuration.

Figure 11:
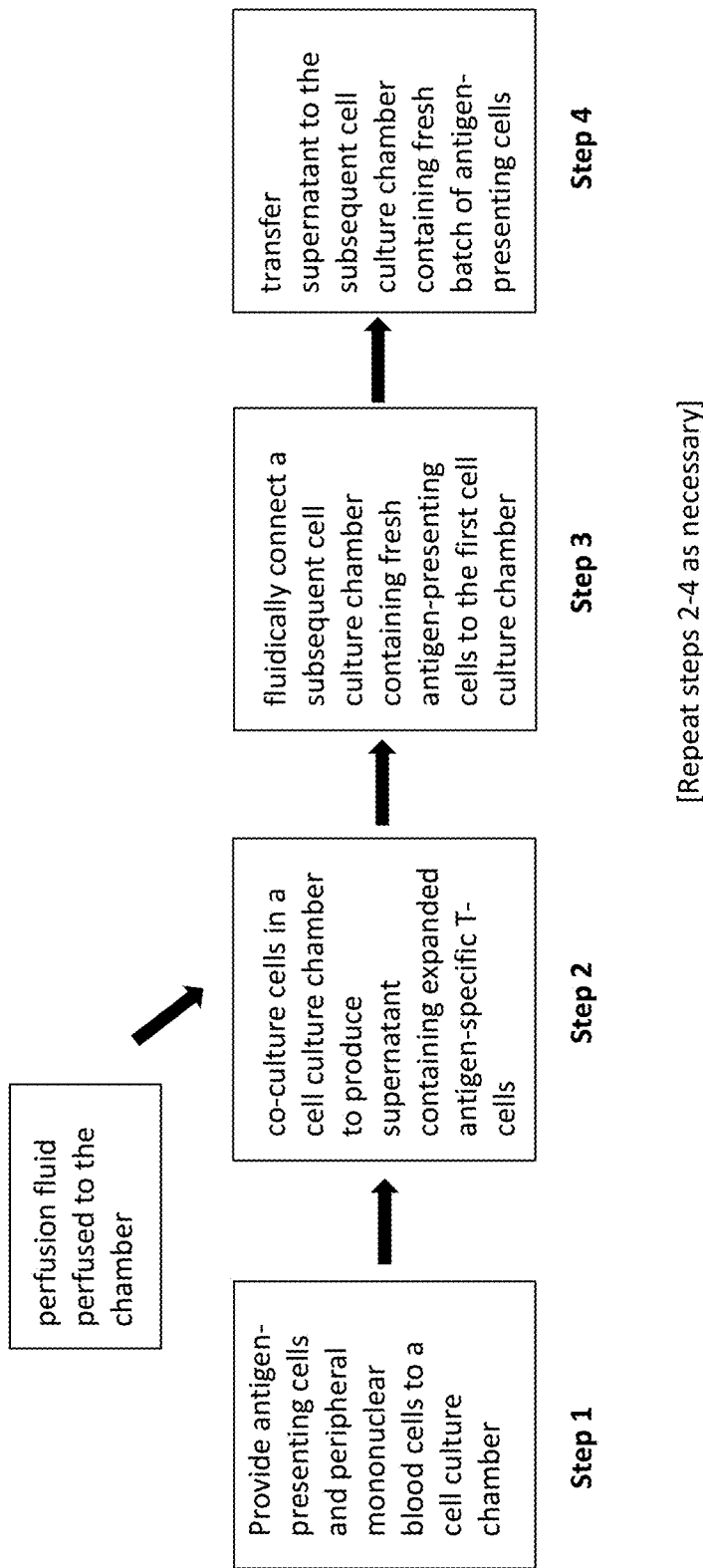
FIG. 11 shows a method for forming cell-based immunotherapeutic products.

Reference is made to FIG. 11 which shows a general overview of a process for forming cell-based immunotherapeutic products. The steps in generating cellular therapeutic product in accordance with certain embodiments of the present invention include the co-culturing of stimulated antigen-presenting cells (e.g. DCs) with T cell containing cells in a biological reactor containing a cell culturing chamber. A supernatant containing expanded therapeutic T cell products is generated during culturing. In certain aspects, in order to produce a quantity of antigen-specific T cells sufficient to elicit a therapeutic response in a patient, the T cells must undergo additional culturing in one or more additional cell culturing chambers. In order to effectuate this additional culturing, the transfer of supernatant from the culture chamber in which the supernatant was generated to a subsequent cell culture chamber containing a fresh supply of antigen-presenting cells must occur. The transfer of supernatant between cell culture chambers may involve the introduction of a gas flow into the first cell culture chamber that transfers the supernatant comprising the first cell product through a fluidic connector and into the new cell culture chamber. Furthermore, during each of the culturing steps, perfusion fluid containing, for example, medium and cytokines, can be perfused to the chambers. In certain aspects, the perfusion fluid flows through the chambers along a vertical flow path so as to ensure that the cells remain within the chamber during culturing. One or more subsequent cell culture chambers can be connected to the system with each chamber containing a new batch of antigen peptide-pulsed autologous antigen-presenting cells.

In order to stimulate and expand antigen-specific T cells, the process begins with a co-culture of T cell containing cells with antigen-presenting cells (APCs) obtained from the same individual in a cell culture chamber. In a particular embodiment, the T cell containing cells include peripheral blood mononuclear cells (PBMCs) and the APCs include DCs. The T cell containing cells and APCs can be provided to the cell culture chamber in a ratio (T-cell containing cells:APCs) from about 1000:1 to 1:1000 of about, such as, for example and not limitation, 1000:1, 900:1, 800:1, 700:1, 600:1, 500:1, 400:1, 300:1, 200:1, 100:1, 75:1, 50:1, 25:1, 20:1, 15:1, 10:1, 5:1, 4:1, 3:1, 2:1, 1:1, 1:2, 1:3, 1:4, 1:5, 1:6, 1:7, 1:8, 1:9, 1:10, 1:15, 1:20, 1:50, 1:75; 1:100, 1:200: 1:300, 1:400, 1:500, 1:600, 1:700, 1:800, 1:900, 1:1000, or any ratio therebetween. In one aspect, a ratio of 10:1 is preferred.

In order to initiate stimulation and expansion of T cells from the interaction of APCs with T-cell containing cells, the APCs need to be stimulated. This can be done through the use of one or more stimulatory molecules. In certain embodiments, the stimulatory molecule is non-tumor specific. In other embodiments, the stimulatory molecule is tumor specific. For example, the stimulatory molecule can be chosen from one or more characteristics of an individual's tumor, such as different antigen peptides. In some embodiments, the stimulatory molecule is preferably added only in the beginning of a culturing cycle. The stimulatory molecule can be added over a period of only about a few minutes, an hour, a few hours, or longer. In one preferred embodiment, the stimulatory molecules are added over about an hour time period.

The co-culturing of APCs and T-cells takes place in a culture medium. Example culture media include, but are not limited to, RPMI medium, and Cellgenix® medium. Any other suitable culture medium known in the art can be used in accordance with embodiments of the present invention. Cytokines such as IL-4 and GM-CSF can also be added to the culture medium.

It is not usually sufficient to do only one co-culture. The disclosed system allows T cells to be pulled out in a suspension. Here T cells can be re-stimulated with fresh dendritic cells and multiple co-cultures can be done in the closed system. With the parallel processing methods of the present invention, the cartridges can be connected in a chain and cells can be pushed from one cartridge to another. One reactor containing mature, adhered DCs will be loaded with PBMCs and subjected to a stimulation cycle with perfusion of medium and cytokines. With parallel processing, the expanded T-cells can be continuously exposed to fresh DCs being produced in the first cell culture chamber by being pulsed with antigen peptides. The stimulation process can continue for as long as needed in order to generate a sufficiently large number of cells for a therapeutic dose of T cells.

Connecting multiple chambers together via a sterile connection can involve the configuration of multiple chambers as discussed above with respect to FIG. 3. The connection allows for the injection of sterile air into the first cell culture chamber to transfer the supernatant containing the expanded T-cells into the second cell culture chamber. In certain embodiments, the one or more biological reactors can be provided in a system containing modules for effectuating various other processes prior to, concurrent with, or subsequent to the process occurring within the cell culture chambers of the biological reactors.

One cartridge can be transferred into harvesting bag or into a new cartridge via sterile welding and sealing. In some embodiments, dendritic cells can be generated and then harvested and cryopreserved, and used on demand. Meanwhile, the system can independently run a second cartridge for fresh dendritic cell generation.

In certain aspects, computational modeling approaches are used to optimize the interaction of T-cells with antigen-presenting cells. Computational models in accordance with the present invention take into account the impacts of perfusion and the optimal time required for stimulation, and incorporate both particle interaction-based as well as kinetic parameter-based approaches. Example particle interaction-based and kinetic parameter-based approaches are known in the art, some of which are described herein. For example, with respect to particle interaction-based approaches, Day and Lythe describe the time required for a T cell to find an APC on the surface of a lymph node using the following expression, where D is the diffusivity of the T cell, and b is the radius of the APC located centrally within a spherical lymph node of radius R. See Day et al., Mathematical Models and Immune Cell Biology; 2011

$$\tau' = \frac{1}{\frac{4}{3}\pi(R^3 - b^3)} \int_b^R 4\pi r^2 F(r) dr = \frac{R^3}{3Db} - \frac{3}{5}\frac{R^2}{D} + \frac{2}{3}\frac{b^2}{D} + \cdots$$

With respect to kinetic parameter-based approaches, Valitutti has developed a model of the interactions between T-cells and antigen-presenting cells, as shown in FIG. 9. Valitutti et al., FEBS Lett. 2010. However, such interactions have not been modeled within the context of a culture chamber or bioreactor.

By incorporating both particle interaction-based as well as kinetic parameter-based approaches into the computational models of the present invention, automated determination and monitoring of the optimal perfusion rate of a perfusion fluid (e.g., cytokine infused medium) for maximizing the probability of two cell types contacting each other within the cell culture chamber can be achieved.

For example, in certain embodiments, a cell culture system is provided that includes a cell culture chamber and a central processing unit comprising memory containing instructions executable by the central processing unit. In certain aspects, the instructions cause the system to receive as a first input data comprising a size of the cell culture chamber, receive as a second input data comprising a first concentration of a first cell type and a second concentration of a second cell type in one or more fluids that will be introduced into the cell culture chamber, and calculate, based on the first and second inputs, a perfusion rate of a perfusion fluid that will be introduced into the cell culture chamber that maximizes a probability of the first cell type and the second cell type contacting each other within the cell culture chamber. Additional details regarding computer systems for implementing the methods of the present invention within cell culture systems are provided below.

In some aspects, the system also includes one or more pumps operably coupled to one or more perfusion fluid reservoirs and operably coupled to the central processing unit, such that the central processing unit also controls the perfusion rate of the perfusion fluid by controlling the one or more pumps.

Recycling Medium

Cell culture medium and supplements (such as cytokines) are expensive, and used medium often has residual nutrients in it, which get discarded. Recognizing this, the disclosed systems provide ways to recapture some of the partially used medium and recycle it. In certain methods of the invention, cells are cultured in one of the disclosed cell culture chambers, wherein cell culture medium is flowed through the cell culture chamber. Generally the fluid flows into an inlet and out of an outlet. A portion of the cell culture medium that has already flowed through the cell culture chamber and out of the outlet is recycled back into the cell culture chamber during the cell culturing process.

In order to determine how much and/or which portion of used medium should be returned to the cell culture chamber, the invention measures one or more parameters such as nutrient content or pH of the used medium prior to recycling. The measured nutrients can be glucose, lactate, dissolved oxygen, or cell metabolites. The parameter of interest is measured and a processor determines whether the parameter meets a predetermined threshold that indicates that it can be recycled. If so, the medium is sent back into the cell culture chamber.

The used medium can be recycled on its own or it can be combined with a bolus of fresh medium. If, on the other hand, the used medium does not meet the predetermined threshold, it is discarded. In some embodiments a valve operates to direct the used medium either to a waste reservoir or back into the cell culture chamber.

In various embodiments, the recycling can be performed at any frequency. For example, the one or more sensors can check the used medium at regular intervals, such as every second, every minute, every 10 minutes, every hour, etc. In other embodiments, the one or more sensors can operate continuously by measuring the medium as it goes through a waste line. In some embodiments, the recycling is controlled through feedback from external filters or sensors that monitor the waste medium to determine if it can be reused or if it is spent. In some embodiments, an in-line sensor is embedded in the system to monitor waste medium and determine if it can be recycled.

Recycling achieves the goal of enabling gas exchange between the exterior of the cell culture chamber and the cells contained within while reducing the amount of medium that would be consumed by the process relative to a process where the medium was being perfused straight through without recycling.

The rate of recycle can be modulated on the basis of required gas exchange and nutrient supply. For example, in a cell culture process where T cells are expanded from a small number to a much larger number, the initial stage of the culture can be carried out at low flow rate perfusion with 100% recycle. This is because the nutrients in the closed perfusion loop are adequate for the small number of cells and the flow rate is set to be sufficient to ensure enough gas exchange (oxygen in, CO2 out). Then, as the cells start to expand, their need for nutrients and gas exchange grows. Growth is monitored and can form the basis of decisions associated with increasing perfusion flow rate (to increase gas exchange) and changing the extent of recycle (recycle only a portion of the medium and add new medium in progressively increasing fractions). In principle, this could be done dynamically and automatically.

In embodiments, the cell culture chamber includes one or more sensors operably coupled to the cell culture chamber. The system can be configured with various sensor configurations to monitor different parameters and integrate with the control system. The sensors may be capable of measuring one or more parameters within the cell culture chamber, such as pH, dissolved oxygen, total biomass, cell diameter, glucose concentration, lactate concentration, and cell metabolite concentration. The system can be customized with off-the-shelf single use sensors for glucose and lactate that sample the perfusion effluent fluid and transmit data. In some embodiments, the cartridges are optically clear and can be interfaced with sensing modalities such as optical density or Raman. In some embodiments the sensors may be operably coupled to a waste line or a waste reservoir, and are configured to measure one or more parameters of the fluid that flows therein. In certain aspects, the one or more sensors are operably coupled to a computer system having a central processing unit for carrying out instructions, such that automatic monitoring and adjustment of parameters is possible. The system may be configured to automatically redirect a fluid back into a chamber via an inlet if the fluid meets a certain parameter. In some embodiments, instrumentation interfaces with a control system architecture using computers, networks, and graphical user interfaces for process management and other peripheral devices to interface with process plant machinery. The waste tube may have a valve that can direct the fluid to one location or another depending on whether the fluid has a sufficient level of nutrients, for example. Additional details regarding computer systems for implementing methods of the present invention using the cell culture chambers is provided below.

Systems Architecture

Aspects of the present disclosure described herein, such as control of the movement of fluid through the system, as described above, and the monitoring and controlling of various parameters, can be performed using any type of computing device, such as a computer or programmable logic controller (PLC), that includes a processor, e.g., a central processing unit, or any combination of computing devices where each device performs at least part of the process or method. In some embodiments, systems and methods described herein may be performed with a handheld device, e.g., a smart tablet, a smart phone, or a specialty device produced for the system.

Methods of the present disclosure can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer program include, by way of example, both general and special purpose microprocessors, and any one or more processor of any kind of digital computer. Generally, a processor will receive instructions and data from a read-only memory or a random access memory or both. Elements of computer are a processor for executing instructions and one or more memory devices for storing instructions and data. Generally, a computer will also include, or be operatively coupled to receive data from or transfer data to, or both, one or more non-transitory mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through network by any form or medium of digital data communication, e.g., a communication network. Examples of communication networks include cell network (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to embodiments of the invention involves transforming a tangible, non-transitory, computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification tags or chips, or any other medium which can be used to store the desired information and which can be accessed by a computing device.

As one skilled in the art would recognize as necessary or best-suited for performance of the methods of the invention, a computer system or machines employed in embodiments of the invention may include one or more processors (e.g., a central processing unit (CPU) a graphics processing unit (GPU) or both), a main memory and a static memory, which communicate with each other via a bus.

Figure 12:
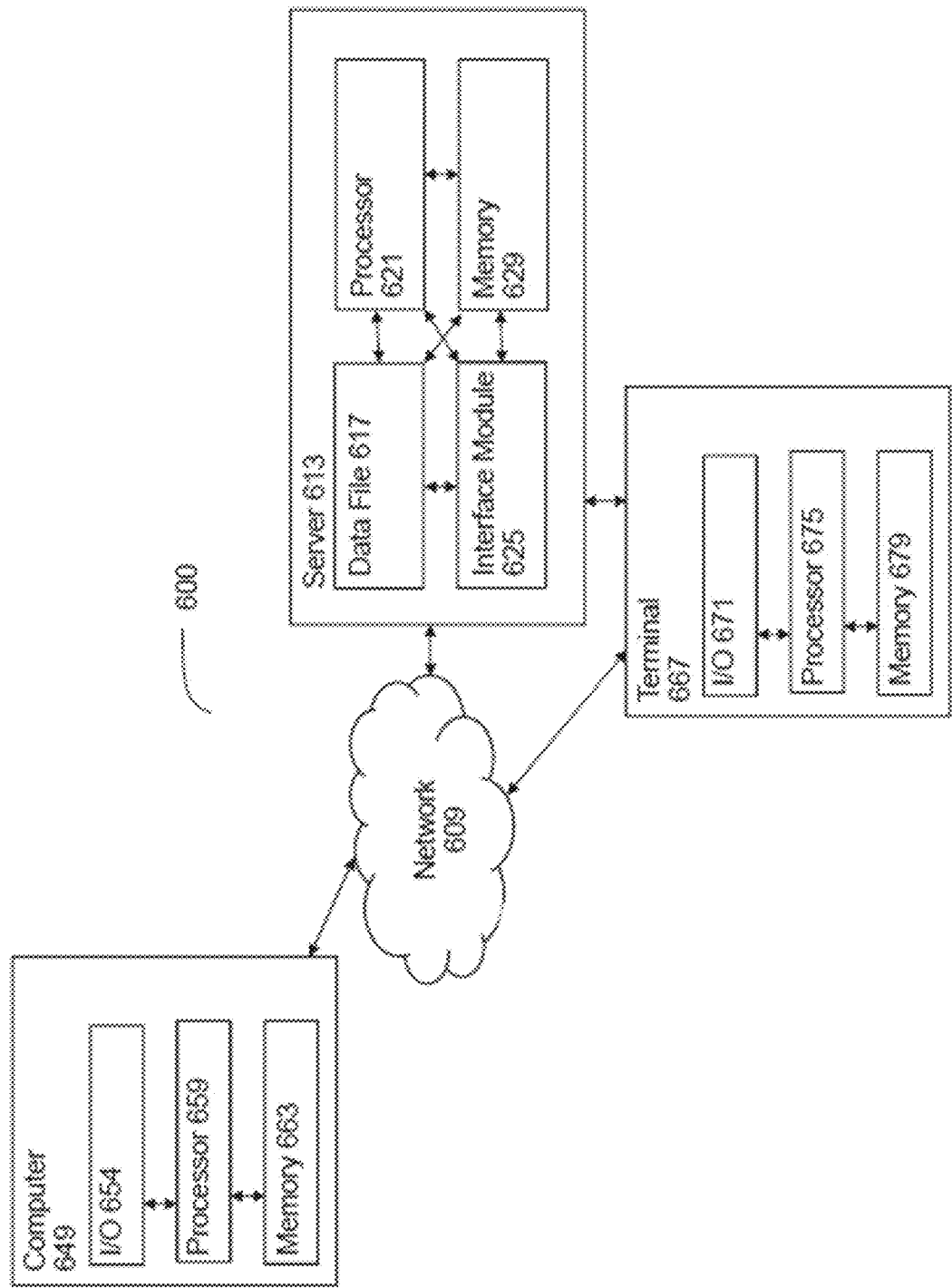
FIG. 12 shows a system architecture according to some embodiments.

In an example embodiment shown in FIG. 12, system 600 can include a computer 649 (e.g., laptop, desktop, or tablet). The computer 649 may be configured to communicate across a network 609. Computer 649 includes one or more processor 659 and memory 663 as well as an input/output mechanism 654. Where methods of the invention employ a client/server architecture, operations of methods of the invention may be performed using server 613, which includes one or more of processor 621 and memory 629, capable of obtaining data, instructions, etc., or providing results via interface module 625 or providing results as a file 617. Server 613 may be engaged over network 609 through computer 649 or terminal 667, or server 613 may be directly connected to terminal 667, including one or more processor 675 and memory 679, as well as input/output mechanism 671.

System 600 or machines according to example embodiments of the invention may further include, for any of I/O 649, 637, or 671 a video display unit (e.g., a liquid crystal display (LCD) or a cathode ray tube (CRT)). Computer systems or machines according to some embodiments can also include an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Memory 663, 679, or 629 according to example embodiments of the invention can include a machine-readable medium on which is stored one or more sets of instructions (e.g., software) embodying any one or more of the methodologies or functions described herein. The software may also reside, completely or at least partially, within the main memory and/or within the processor during execution thereof by the computer system, the main memory and the processor also constituting machine-readable media. The software may further be transmitted or received over a network via the network interface device.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

While the present invention has been described in conjunction with certain embodiments, one of ordinary skill, after reading the foregoing specification, will be able to effect various changes, substitutions of equivalents, and other alterations to the compositions and methods set forth herein.

What is claimed is:

1. A method for producing neoantigen-targeting T cells, the method comprising:
providing a cell culture instrument comprising a gas-impermeable first cell culture chamber containing purified monocytes, wherein the first cell culture chamber is fluidically connected to a gas-impermeable second cell culture chamber containing purified T cells, one or more pumps, a fluid reservoir, a waste reservoir, and one or more gas permeable tubes that fluidically connect, via sterile tube welded connections, the fluid reservoir, the waste reservoir, and the first and second gas-impermeable cell culture chambers to at least one of the one or more pumps, and each of the first and second gas-impermeable cell culture chambers to one another;
perfusing the purified monocytes in the first cell culture chamber with cell culture medium to produce dendritic cells;
contacting the dendritic cells with antigen material comprising one or more tumor-specific peptides to thereby produce mature dendritic cells presenting one or more tumor-specific peptides in the first cell culture chamber;
flowing purified T cells from the a second culture chamber into the first cell culture chamber;
co-culturing the purified T cells with the mature dendritic cells to thereby produce a first batch of expanded neoantigen-targeting T cells in the first cell culture chamber to complete a first stimulation cycle; and
generating a second batch of mature dendritic cells in the second cell culture chamber asynchronously from the first batch of mature dendritic cells.

2. The method of claim 1, wherein the one or more tumor-specific peptides are selected from a library of a plurality of tumor-specific peptides.

3. The method of claim 1, wherein the co-culturing step completes a first stimulation cycle.

4. The method of claim 1, further comprising:
introducing the expanded T cells from the first culture chamber into the second cell culture chamber containing the second batch of mature dendritic cells to co-culture the expanded T cells with the second batch of mature dendritic cells to complete a second stimulation cycle.

5. The method of claim 4, wherein the second batch of mature dendritic cells have been stimulated with a different set of peptides than the mature dendritic cells from the first culture chamber.

6. The method of claim 4, further comprising:
transferring the expanded T cells that have been co-cultured with the second batch of mature dendritic cells to a cell culture chamber comprising a third batch of mature dendritic cells to complete a third stimulation cycle.

7. The method of claim 6, wherein the third batch of mature dendritic cells have been stimulated with a different set of peptides than the mature dendritic cells from the second batch.

8. The method of claim 6, wherein the stimulation cycle is repeated from 4 to 25 times.

9. The method of claim 1, wherein the mature dendritic cells are generated from monocytes from a patient.

10. The method of claim 1, wherein the dendritic cells and the T cells are processed in parallel.

11. The method of claim 1, wherein the first and second culture chambers are made of polystyrene.

12. The method of claim 1, wherein the first and second culture chambers are connected via a sterile tube.

13. The method of claim 1, wherein the cell culture medium is provided in sterile vessel and is connected to the closed system by sterile tube welding.

14. The method of claim 1, wherein flowing the cell culture medium into the first culture chamber comprises eliminating headspace in the first culture chamber.

15. The method of claim 1, further comprising:
draining fluid from the first culture chamber;
washing the neoantigen transduced T cells with a buffer; and
flowing a cryopreservation medium into the first culture chamber to re-suspend the neo-antigen transduced T cells.

16. The method of claim 1, further comprising flowing the neoantigen transduced T cells into a harvesting vessel in a closed manner.

17. The method of claim 1, wherein each of the flowing steps is done via sterile tubes.

18. The method of claim 17, wherein the sterile tubes are connected by sterile tube welding.

* * * * *